US009801544B2

(12) United States Patent
Norita

(10) Patent No.: US 9,801,544 B2
(45) Date of Patent: Oct. 31, 2017

(54) MONITOR SUBJECT MONITORING DEVICE AND METHOD, AND MONITOR SUBJECT MONITORING SYSTEM

(71) Applicant: Konica Minolta, Inc., Chiyoda-ku (JP)

(72) Inventor: Toshio Norita, Mishima-gun (JP)

(73) Assignee: Konica Minolta, Inc., Tokyo (JP)

( * ) Notice: Subject to any disclaimer, the term of this patent is extended or adjusted under 35 U.S.C. 154(b) by 0 days.

(21) Appl. No.: 15/021,472

(22) PCT Filed: Apr. 28, 2014

(86) PCT No.: PCT/JP2014/061832
§ 371 (c)(1),
(2) Date: Mar. 11, 2016

(87) PCT Pub. No.: WO2015/037269
PCT Pub. Date: Mar. 19, 2015

(65) Prior Publication Data
US 2016/0220114 A1 Aug. 4, 2016

(30) Foreign Application Priority Data
Sep. 13, 2013 (JP) ................................. 2013-190185

(51) Int. Cl.
G08C 19/22 (2006.01)
A61B 5/00 (2006.01)
(Continued)

(52) U.S. Cl.
CPC ............ *A61B 5/002* (2013.01); *A61B 5/0026* (2013.01); *G08B 21/02* (2013.01); *G08B 21/0476* (2013.01); *G08B 25/04* (2013.01)

(58) Field of Classification Search
CPC ...... A61B 5/002; A61B 5/0026; G08B 21/02; G08B 21/0476
See application file for complete search history.

(56) References Cited

U.S. PATENT DOCUMENTS 6,106,463 A * 8/2000 Wilk ...................... A61B 5/742
600/437
6,319,201 B1 * 11/2001 Wilk .................... A61B 5/6843
600/437

(Continued)

FOREIGN PATENT DOCUMENTS

JP 2009-268854 11/2009
JP 2010-539617 12/2010

(Continued)

*Primary Examiner* — Joseph Feild
*Assistant Examiner* — Rufus Point
(74) *Attorney, Agent, or Firm* — Cozen O'Connor

(57) ABSTRACT

Disclosed are a monitor subject monitoring apparatus, a monitor subject monitoring method, and a monitor subject monitoring system configured to determine a first body state of a subject, based on an image data of the subject, and to determine a second body state of the subject, based on physiological data of the subject, wherein the subject monitoring apparatus, the subject monitoring method and the subject monitoring system are operable, when it is determined that one of the first and second body states of the subject is not abnormal, to re-perform a corresponding one of the determinations, and then determine whether or not a notification indicating that the subject is in an abnormal state should be issued, based on a result of the re-performed determination about the one of the first and second body states.

11 Claims, 7 Drawing Sheets

(51) Int. Cl.
*G08B 21/02* (2006.01)
*G08B 25/04* (2006.01)
*G08B 21/04* (2006.01)

(56) References Cited

U.S. PATENT DOCUMENTS

| | | | | |
|---|---|---|---|---|
| 7,502,498 | B2* | 3/2009 | Wen | G06F 19/3418 128/922 |
| 7,567,200 | B1* | 7/2009 | Osterweil | A61B 5/1117 340/573.1 |
| 7,942,526 | B2* | 5/2011 | Gierhart | A61B 3/12 351/205 |
| 8,323,189 | B2* | 12/2012 | Tran | A61B 5/0024 600/300 |
| 2005/0131292 | A1* | 6/2005 | Huss | A61B 5/0476 600/430 |
| 2006/0056655 | A1* | 3/2006 | Wen | G06F 19/3418 382/103 |
| 2007/0096927 | A1* | 5/2007 | Albert | G08B 1/08 340/573.1 |
| 2007/0197881 | A1* | 8/2007 | Wolf | A61B 5/0002 600/300 |
| 2008/0167535 | A1* | 7/2008 | Stivoric | G01R 29/0814 600/301 |
| 2008/0319282 | A1* | 12/2008 | Tran | A61B 5/103 600/301 |
| 2009/0281414 | A1* | 11/2009 | Feldman | A61B 5/04005 600/409 |
| 2010/0130873 | A1* | 5/2010 | Yuen | A61B 5/0205 600/484 |
| 2010/0191077 | A1* | 7/2010 | O'Kane | A61B 5/164 600/306 |
| 2010/0261980 | A1 | 10/2010 | Peng et al. | |
| 2010/0286490 | A1* | 11/2010 | Koverzin | G06F 19/3418 600/301 |
| 2012/0101411 | A1* | 4/2012 | Hausdorff | A61B 5/1117 600/595 |
| 2012/0218123 | A1* | 8/2012 | Ji | A61B 5/7232 340/870.07 |
| 2013/0072807 | A1* | 3/2013 | Tran | A61B 5/02405 600/485 |
| 2013/0100268 | A1* | 4/2013 | Mihailidis | G08B 21/02 348/77 |
| 2013/0221746 | A1 | 8/2013 | Nakayama | |
| 2014/0036647 | A1 | 2/2014 | Yoshizawa et al. | |
| 2015/0179039 | A1 | 6/2015 | Miwa | |
| 2015/0229773 | A1 | 8/2015 | Miwa | |

FOREIGN PATENT DOCUMENTS

| | | |
|---|---|---|
| JP | 2011-66632 | 3/2011 |
| JP | 2012-075861 | 4/2012 |
| JP | 2012-097670 | 5/2012 |
| JP | 4989172 | 8/2012 |
| JP | 5278981 | 9/2013 |

* cited by examiner

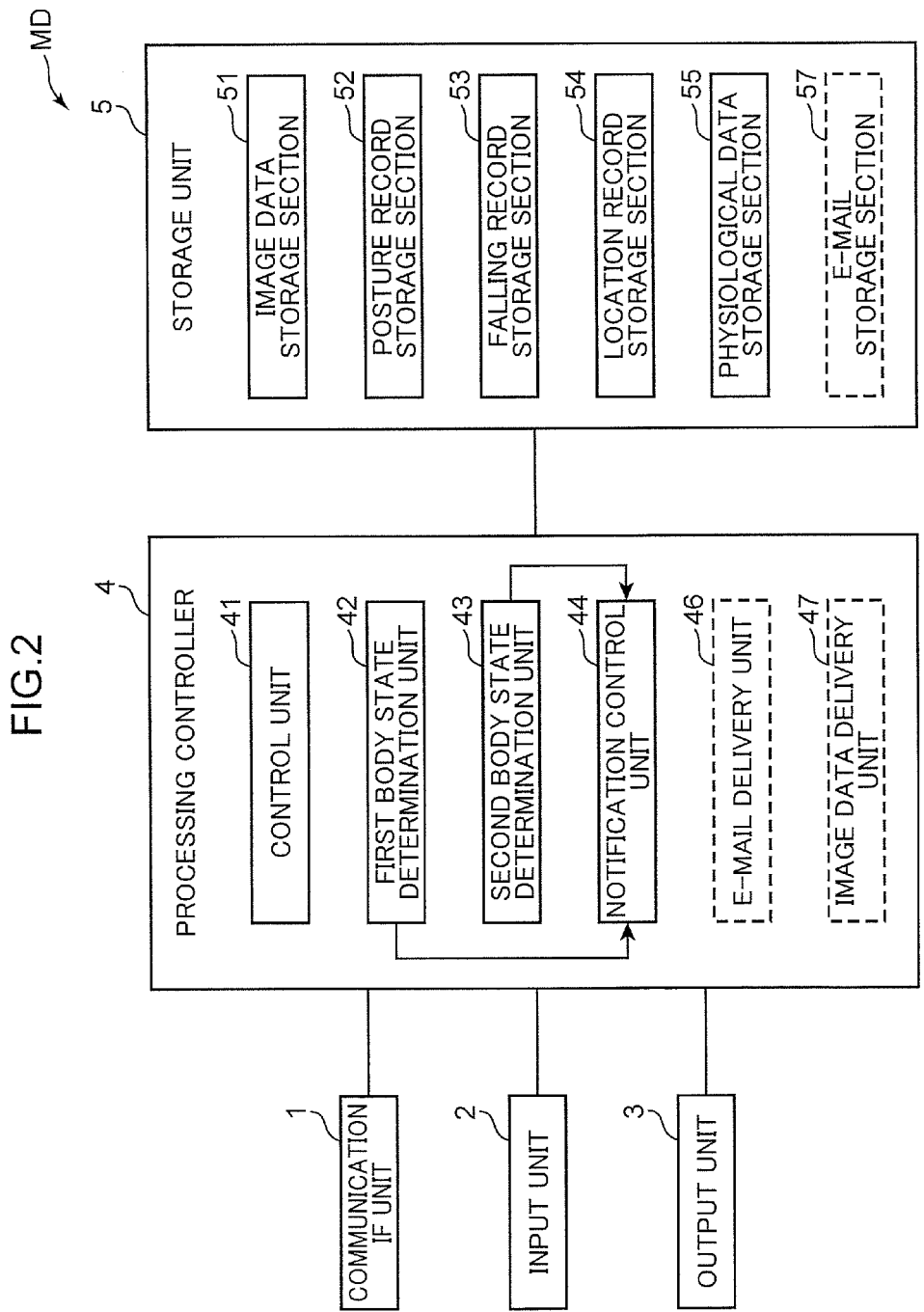

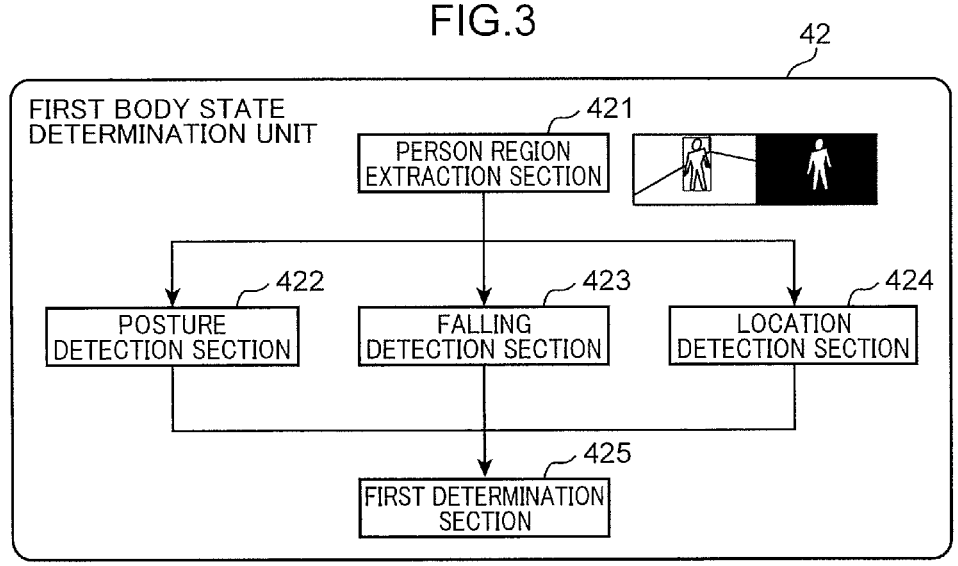
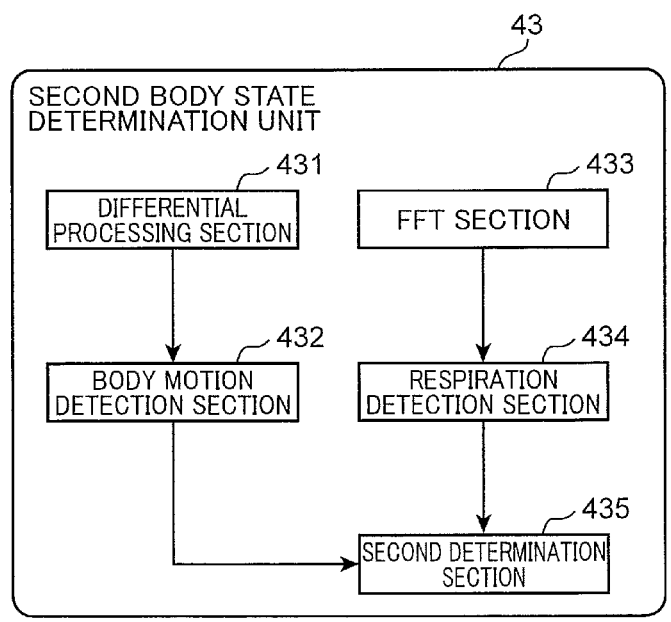

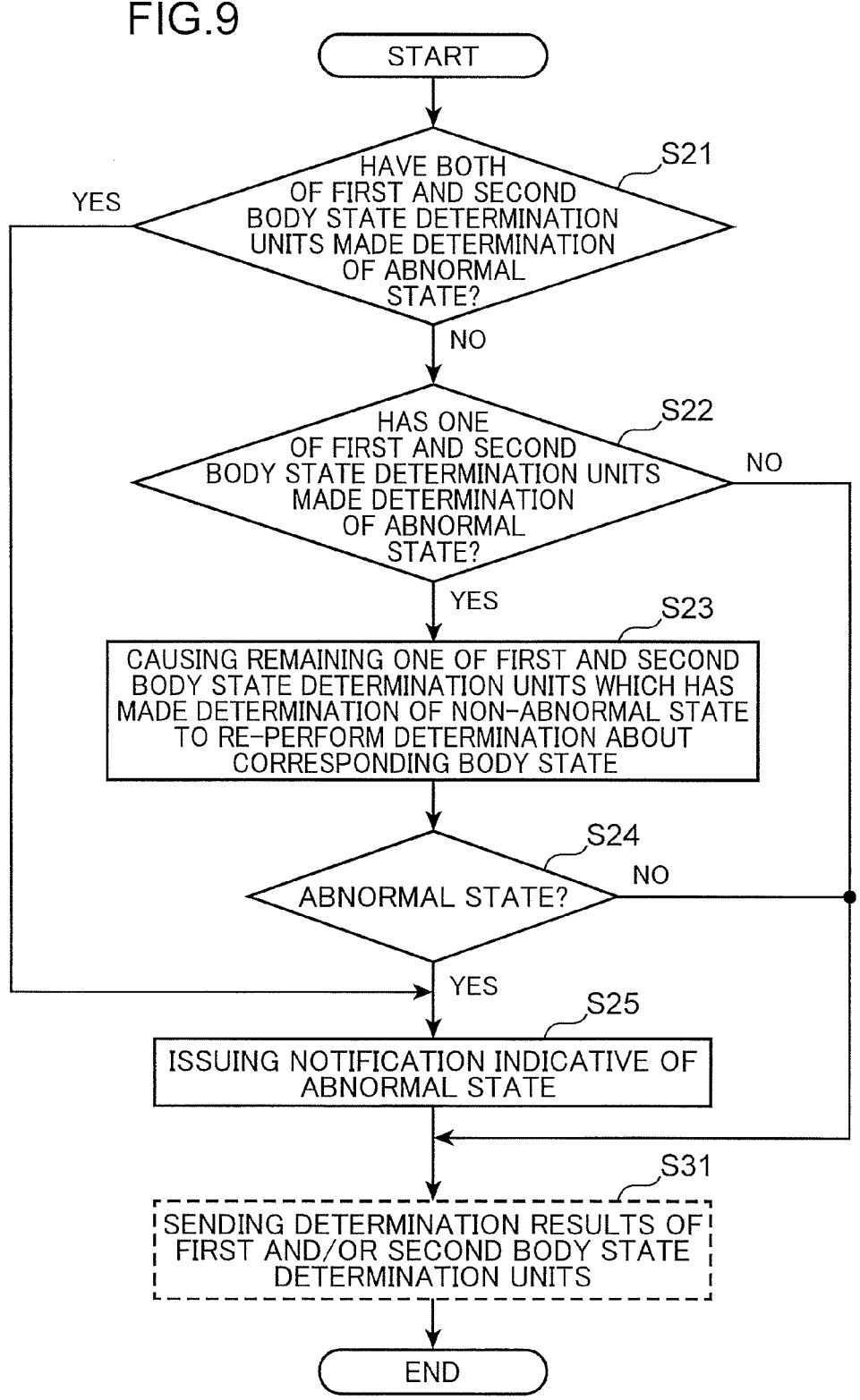

MONITOR SUBJECT MONITORING DEVICE AND METHOD, AND MONITOR SUBJECT MONITORING SYSTEM

RELATED APPLICATIONS

This is a U.S. National Phase Application under 35 USC 371 of International Application PCT/JP2014/061832 filed on Apr. 28, 2014.

This application claims the priority of Japanese application no. 2013-190185 filed Sep. 13, 2013, the entire content of which is hereby incorporated by reference.

TECHNICAL FIELD

The present invention relates to a subject monitoring apparatus, a subject monitoring method and a subject monitoring system for monitoring a subject to be monitored, i.e., a monitoring target person, and, when it is determined that a given abnormality occurs in the subject, issuing a notification indicative of this fact.

BACKGROUND ART

As one example, in Japan, as a result of a rise in living standards, an improvement in hygienic environment and a rise in level of medical treatment along with rapid economic growth after World War II, Japan is entering into an aged society, more specifically, a super-aged society in which a population aging rate, i.e., a ratio of a population of persons over 65 to a total population, is greater than 21%. Further, there are forecasts that, in 2020, the population of persons over 65 will reach about 34.56 million in a total population of about 124.11 million, while, in 2005, the population of persons over 65 was about 25.56 million in a total population of about 127.65 million.

In such an aged society, it is forecast that the number of persons requiring nursing care due to disease, injury and the like becomes greater than that in a non-aged or normal society.

Such a person requiring nursing care enters or gets a place on a facility such as a hospital or a welfare facility for the aged (e.g., in Japan, a respite care facility for the aged, a nursing home for the aged or a special nursing home for the aged), and receives nursing care. This type of facility such as a hospital or a welfare facility for the aged is generally equipped with a so-called nurse call system to be used when a person requiring nursing care calls a nurse or a care worker to receive nursing care. The facility is also equipped with a device for monitoring a state of the person requiring nursing care, as needed basis.

One example of the nurse call system is disclosed in the following Patent Literature 1. A nurse call system disclosed in the Patent Literature 1 includes: an in-bed child unit installed in each bed in each hospital room of a hospital or a welfare facility for the aged, and configured to allow a person receiving nursing care to call a nurse, and a plate-shaped child unit detachably connected to the in-bed child unit; a call-corresponding camera (30a, 30b, - - - ) installed in each hospital room and configured to take an image of the person; a nurse call parent unit installed in a nurse center and configured to detect a call from the in-bed child unit and inform a nurse of the call so as to allow the nurse who acknowledged the call to establish communication, wherein the nurse call parent unit is connected with an external call-corresponding monitor for outputting the image of the subject taken by the call-corresponding camera, and wherein the external call-corresponding monitor is connected with the call-corresponding camera and configured to be controlled by the nurse call parent unit when the nurse call parent unit detects the call from the in-bed child unit; a storage unit storing therein a camera selection table for selecting one of a plurality of the call-corresponding cameras which has a camera number corresponding to a child unit number of the plate-shaped child unit connected to the in-bed child unit as a source of the call; and a camera drive circuit for reading, from the storage section, the camera number corresponding to the child unit number of the plate-shaped child unit connected to the in-bed child unit as the source of the call, and driving the call-corresponding camera having the read camera number to output an image of the person to the external call-corresponding monitor.

One example of a system for monitoring a state of the person requiring nursing care is disclosed in the following Patent Literature 2. A system disclosed in the Patent Literature 2 is a monitoring system for monitoring an abnormal state of a target body, which includes: a physiological signal monitor configured to monitor a physiological signal; a processor configured to receive an output signal from the physiological signal monitor and detect the occurrence of abnormality in the physiological signal; and a detection sub-system coupled to receive an output signal from the processor, and configured to operate in a selected detection mode for monitoring a movement of the target body, based on the output signal from the processor, so as to detect the abnormal state. In order to perform an initial determination about a possibility of fall-over of a user, the physiological signal is continuously measured in view of a causal factor of the fall-over (see, for example, paragraph [0021]). More specifically, the physiological signal is heart rate, blood flow pulsation, blood pressure, ECG, EMG or $SpO_2$ (see, for example, paragraph [0026]). The Patent Literature 2 also describes that, in order to detect abnormality in a target body, the monitoring system may further include an accelerator meter for detecting an acceleration of the target body, or an inclination sensor for measuring a level of inclination of the target body, and that the abnormality in the target body may be detected from an output signal from the accelerator meter or the inclination sensor, while taking into account the physiological signal (see, for example, paragraph [0029]).

Meanwhile, in the nurse call system disclosed in the Patent Literature 1, a nurse can view an image of a person receiving nursing care (one example of a subject) taken by the call-corresponding camera, on the external call-corresponding monitor, so that it becomes possible to observe a state of the person without going drown to a room of the person. However, as long as no call (nurse call) is generated from the person based on an operation of the in-bed child unit by the person, an image of the person taken by the call-corresponding camera is never output, so that it is impossible to view the image of the person on the external call-corresponding monitor. As long as no call is generated from the person based on an operation of the in-bed child unit by the person, a nurse cannot know whether or not the person requires nursing care, in the first place.

The monitoring system disclosed in the Patent Literature 2 is capable of detecting fall-over of a target body (one example of a subject). However, the monitoring system disclosed in the Patent Literature 2 is intended to detect fall-over of the target body to thereby select a specific detection mode so as to achieve power saving. That is, the monitoring system disclosed in the Patent Literature 2 is not configured to issue a notification indicative of fall-over of the target body to outside so as to inform a nurse or the like of the fall-over of the target body. Therefor, it is impossible to combine the monitoring system disclosed in the Patent Literature 2 with the nurse call system disclosed in the Patent Literature 1.

Supposing that the nurse call system disclosed in the Patent Literature 1 and the monitoring system disclosed in the Patent Literature 2 can be combined together, an erroneous determination is likely to be undesirably made in the resulting system, because the monitoring system disclosed in the Patent Literature 2 is configured to determine an abnormal state of the target body only or mainly based on the physiological signal although there is the description about using the acceleration meter or the inclination sensor for fall-over.

Although the Patent Literature makes mention of an optical sensor, this optical sensor is designed to detect light and dark of an environment in which the target body is located (present), i.e., is not an image sensor.

Further, in recent years, due to further aging of society, home medical care in which a medical staff visits a patient's home to provide medical care has been gradually increasing, and the number of households of an elderly person living alone has also been increasing. Therefore, it will become necessary to monitor such a patient or single-living person under medical treatment at home.

CITATION LIST

Patent Literature

Patent Literature 1: JP 4989172B (JP 2008-79800A)
Patent Literature 2: JP 2010-539617A

SUMMARY OF INVENTION

The present invention has been made in view of the above circumstances, and an object of the present invention is to provide a subject monitoring apparatus, a subject monitoring method and a subject monitoring system which are capable of, when it is determined that a body state of a subject to be monitored is abnormal, reducing an erroneous determination, and, when it is determined that abnormality occurs in the subject, automatically issuing a notification indicative of the fact.

A subject monitoring apparatus, a subject monitoring method and a subject monitoring system of the present invention are configured to determine a first body state of the subject, based on an image data of the subject, and to determine a second body state of the subject, based on physiological data of the subject, wherein the subject monitoring apparatus, the subject monitoring method and the subject monitoring system are operable, when one of the first and second body states of the subject is determined to be not an abnormal state, to re-perform a corresponding one of the determinations, and then determine whether or not a notification indicating that the subject is in an abnormal state should be issued, based on a result of the re-performed determination about the one of the first and second body states. Therefore, the subject monitoring apparatus, the subject monitoring method and the subject monitoring system of the present invention are capable of, when it is determined that a body state of a subject to be monitored is abnormal, reducing an erroneous determination, and, when it is determined that abnormality occurs in the subject, automatically issuing a notification indicative of the fact.

The above and other objects, features and advantages of the present invention will be apparent from the following detailed description and the accompanying drawings.

BRIEF DESCRIPTION OF DRAWINGS

FIG. 2 is a diagram depicting a configuration of a subject monitoring apparatus in the subject monitoring system depicted in FIG. 1.

FIG. 3 is a diagram depicting a configuration of a first body state determination unit in the subject monitoring apparatus depicted in FIG. 2.

FIG. 4 is a diagram depicting a configuration of a second body state determination unit in the subject monitoring apparatus depicted in FIG. 2.

FIG. 9 is a flowchart depicting an operation of the subject monitoring system in FIG. 1.

DESCRIPTION OF EMBODIMENTS

With reference to the drawings, one embodiment of the present invention will now be described. It should be noted that elements or components assigned with the same reference sign in the figures means that they are identical, and therefore duplicated description thereof will be omitted appropriately. In this specification, for a generic term, a reference sign without any suffix is assigned thereto, and, for a term meaning an individual element or component, a reference sign with a suffix is assigned thereto.

Figure 1:
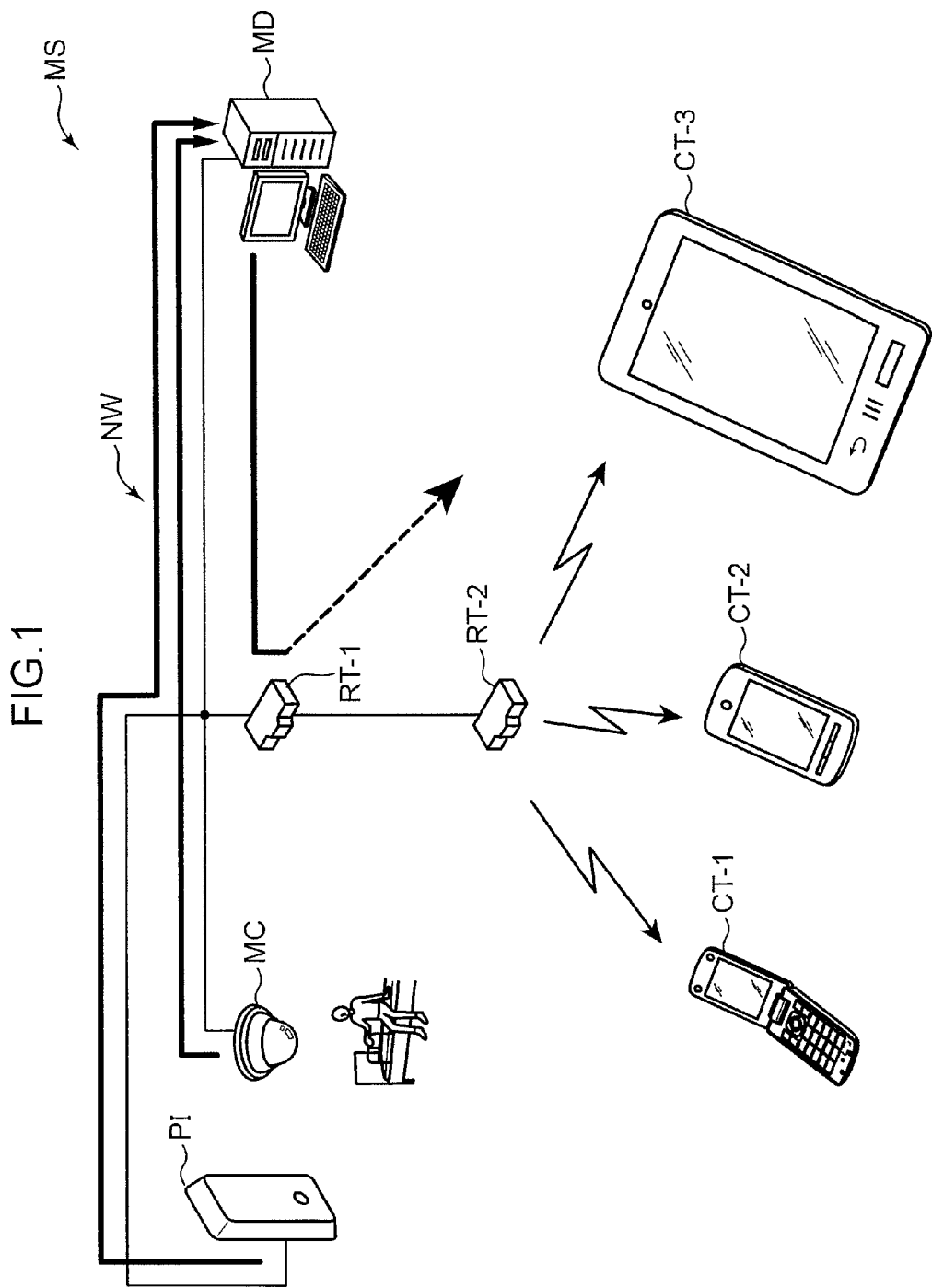
FIG. 1 is a diagram depicting a configuration of a subject monitoring system according to one embodiment of the present invention.
Figure 5:
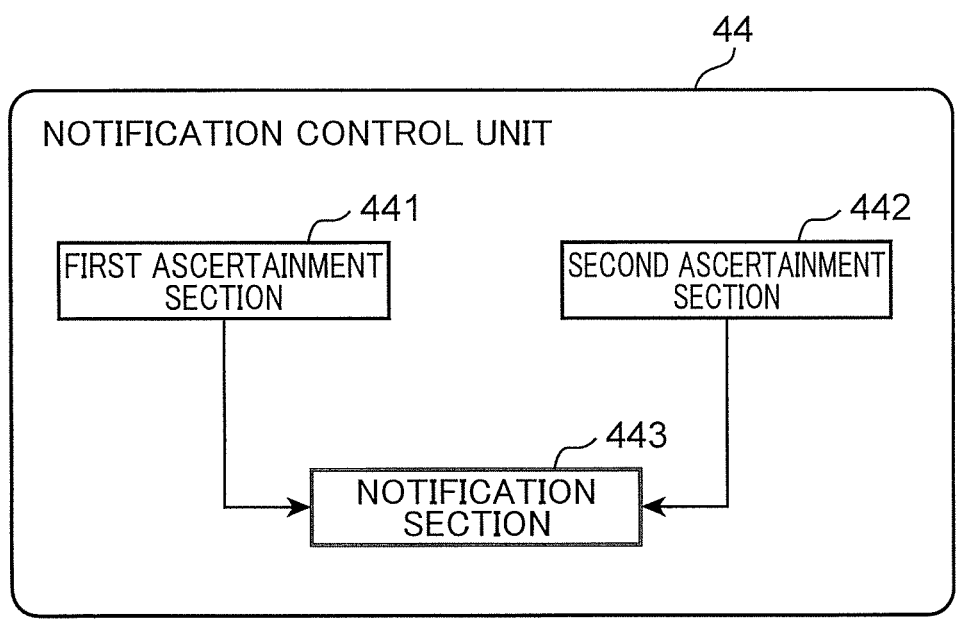
FIG. 5 is a diagram depicting a configuration of a notification control unit in the subject monitoring apparatus depicted in FIG. 2.
Figure 6:
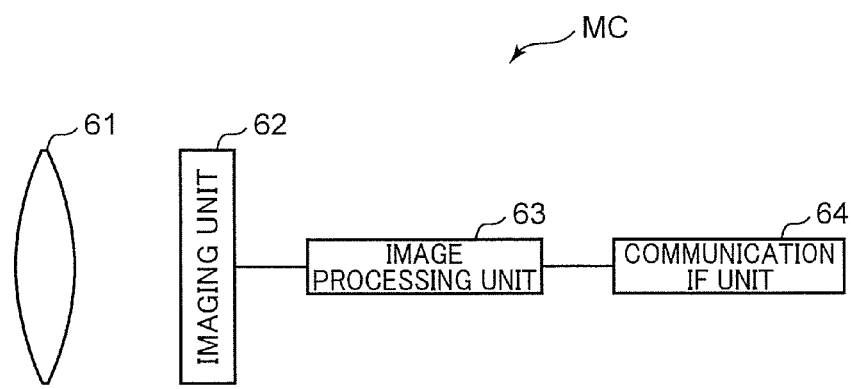
FIG. 6 is a diagram depicting a configuration of an image data generator in the subject monitoring system depicted in FIG. 1.

FIG. 1 is a diagram depicting a configuration of a subject monitoring system according to one embodiment of the present invention. FIG. 2 is a diagram depicting a configuration of a subject monitoring apparatus in the subject monitoring system depicted in FIG. 1. FIG. 3 is a diagram depicting a configuration of a first body state determination unit in the subject monitoring apparatus depicted in FIG. 2. FIG. 4 is a diagram depicting a configuration of a second body state determination unit in the subject monitoring apparatus depicted in FIG. 2. FIG. 5 is a diagram depicting a configuration of a notification control unit in the subject monitoring apparatus depicted in FIG. 2. FIG. 6 is a diagram depicting a configuration of an image data generator in the subject monitoring system depicted in FIG. 1.

The subject monitoring system MS according to this embodiment is designed to monitor a subject to be monitored (watched over) (monitoring (watching) target person). For example, it may include an image data generator MC, a physiological data generator PI and a subject monitoring apparatus MD, as depicted in FIG. 1. In the example depicted in FIG. 1, the subject monitoring system MS further includes one or more communication terminals CT, and a communication network NW. The subject monitoring system MS is provided in an appropriate location depending on a subject. The subject (monitoring (watching) target person) means a person who has to ask someone to find the occurrence of given undesirable states such as an abnormal state, e.g., a person requiring nursing care due to disease, injury and the like, a person requiring nursing care due to a decline in physical performance or the like, or a single-living person. For this purpose, the subject monitoring system MS is suitably provided in a building such as a hospital, a welfare facility for the aged or a dwelling unit, depending on a type of subject. It should be understood that the subject monitoring system MS may be provided in one building such as a hospital or a welfare facility for the aged, in a centralized manner, or may be provided in a plurality of buildings such as a plurality of dwelling units and a monitoring center, in a decentralized manner. In one example, the image data generator MC and the physiological data generator P1 are provided in each hospital room or bed on each floor, and the subject monitoring apparatus MD is provided in a nurse station on the same floor. In another example, the image data generator MC and the physiological data generator P1 are provided in each dwelling unit, and the subject monitoring apparatus MD is provided in a monitoring center. For example, the communication terminal CT is carried by a watcher, or provided in a dwelling unit of the watcher.

The communication network NW is a transmission channel such as a communication line, a telephone network, a digital communication network or a radio communication network, which is configured to communicably connect the image data generator MC, the physiological data generator P1, the subject monitoring apparatus MD and the communication terminals CT to each other, wherein data is transmitted by a communication signal, using a given communication protocol. For example, the communication network NW is composed of an intranet or the Internet, using as the communication protocol, a so-called Internet protocol such as FTP (File Transfer Protocol), TCP/IP (Transmission Control Protocol/Internet Protocol). In this embodiment, the communication network NW is a local area network (LAN) including a wired router RT-1, and a wireless router RT-2, and is configured to communicably connect the image data generator MC, the physiological data generator P1 and the subject monitoring apparatus MD to each other in a wired manner, and communicably connect the subject monitoring apparatus MD and the communication terminals CT to each other in a wireless manner.

The wired router RT-1 is a relay unit connected to each of the image data generator MC, the physiological data generator P1, the subject monitoring apparatus MD and the wireless router RT-2, via a communication wire, and configured to select a communication route depending on a designation of a communication signal (communications packet) and relay the communication signal toward the selected communication route. In this embodiment, PoE (Power over Ethernet) (Ethernet is a trademark) standardized as IEEE Standard 802.3af is utilized, and a PoE distribution cable is used as the communication wire. The wired router RT-1 is configured to feed power to the image data generator MC through the PoE. Therefore, it is possible to install the image data generator MC in a location where it is impossible or difficult to use an electrical outlet or AC power source. The wireless router RT-2 is a relay unit connected to the wireless router RT-1 via a communication wire, and wirelessly connected to the communication terminals CT, and configured to select a communication route depending on a designation of a communication signal (communications packet) and relay the communication signal toward the selected communication route. In the example depicted in FIG. 1, the wired router RT-1 and the wireless router RT-2 are constructed as separate units. Alternatively, they may be integrally constructed. That is the wired router RT-1 may be constructed to additionally have a function of the wireless router RT-2. Further, an appropriate number of routers may be used depending on a scale of the communication network NW.

Each of the communication terminals CT is a device having a communication function and a display function and configured to receive a notification indicating that a subject is in an abnormal state (subject's abnormal state-indicating notification) from the subject monitoring apparatus MD and display the received notification. For example, it may be a mobile phone CT-1, a smartphone CT-2 or a tablet computer CT-3. In this embodiment, the subject's abnormal state-indicating notification is received via e-mail, and, for this purpose, the communication terminal CT is equipped with a mailer for performing creation, sending, receiving, storing and management of e-mails. Further, an image of a subject is received in a streaming manner, and, for this purpose, the communication terminal CT is equipped with a web browser having a streaming function. The subject's image is reproduced while being downloaded, by the web browser, and displayed on a display such as a liquid crystal display or an organic EL display, in the communication terminal CT.

The image data generator MC is a device for generating image data which is data representing an image of a subject. For example, it may be a digital camera such as a so-called web camera. The image data generator MC is disposed such that an imaging (image-taking) direction is coincident with an appropriate direction allowing imaging of a space in which a subject is usually present. In this embodiment, subject's image data is transmitted to the subject monitoring apparatus MD via the communication network NW, and, for this purpose, the image data generator MC has a communication function. This image data generator MC includes an imaging optical system 61, an imaging unit 62, an image processing unit 63, and a communication interface unit (hereinafter abbreviated as "communication IF unit" 64, as depicted, for example, in FIG. 6.

The imaging optical system 61 includes one or more of optical elements (e.g., a lens, a prism or a filter), and is configured to focus an optical image of an object (subject to be imaged) on a light-receiving surface of the imaging unit 62. The imaging unit 62 is a device configured to photoelectrically convert the object's optical image focused by the imaging optical system 61, to R (red) G (green) B (blue) color component signals, and output the signals to the image processing unit 63. For example, the imaging unit 62 includes a CCD image sensor or a CMOS image sensor. The image processing unit 63 is a circuit connected to the imaging unit 62 and configured to subject the R (red) G (green) B (blue) color component signals obtained by the imaging unit 62 to given image processing to produce image data. For example, it may include DSP (Digital Signal Processor) and a peripheral circuit thereof. For example, the given image processing is well-known image processing such as: amplification processing and digital conversion processing to be performed for an analog output signal from the imaging unit 62; processing for determining a black level appropriate to the entire image; γ-correction processing; white balance adjustment (WB adjustment) processing; contour correction processing; or color unevenness correction processing. The communication IF unit 64 is an interface connected to the image processing unit 63 and configured to send and receive a communication signal with respect to the subject monitoring apparatus MD therethrough via the communication network NW. For example, it may be a network card such as a LAN card.

In this image data generator MC, an object's optical image is led to the light-receiving surface of the imaging unit 62 along an optical axis of the imaging optical system 61 through the imaging optical system 61, and then imaged by the imaging unit 62. Subsequently, through the image processing unit 63, the imaged object's optical image is subjected to image processing and thereby formed as image data. Then, the image data is superimposed on a communication signal, and transmitted as subject's image data to the subject monitoring apparatus MD through the communication IF unit 64.

The physiological data generator P1 is a device for generating physiological data which is data representing physiological information of a subject. The physiological data generator P1 is disposed to be allowed to collect physiological data of a subject. In this embodiment, the physiological data is transmitted to the subject monitoring apparatus MD via the communication network NW, and, for this purpose, the physiological data generator P1 has a communication function. Examples of the physiological information include respiratory rate, heart rate, blood flow pulsation, blood pressure, ECG (Electrocardiogram), EMG (Electromyogram) or $SpO_2$ (blood oxygen level). In the aforementioned Patent Literature 2, these are referred to as "physiological signals". However, in this specification, they are referred to as "physiological information", as mentioned above, in order to avoid confusion with "signal" as the "communication signal". The blood pressure, the electrocardiogram, the electromyogram and the blood oxygen level are measured, respectively, by a blood-pressure meter, an electrocardiograph, an electromyograph and a pulse oxymeter, and the heart rate is measured by the blood-pressure meter, the pulse oxymeter or the like. The physiological data generator P1 may be a device such as a blood-pressure meter, an electrocardiograph, an electromyograph and a pulse oxymeter, as mentioned above. In this embodiment, such a device is divided into: a probe unit (sensor unit) for measuring a given physical amount based on physiological activities of a subject to generate measurement data; and a signal processing unit for subjecting the measurement data obtained by the probe unit to signal processing to obtain physiological information. Thus, the physiological data generator P1 has such a probe unit. In this embodiment, the signal processing unit is incorporated into the subject monitoring apparatus MD as a part of an aftermentioned second body state determination unit 43. In one example, the physiological data generator P1 is composed of a cuff in a blood pressure meter, wherein it is operable to measure a pressure, and the signal processing unit is operable to obtain a blood-pressure value from the measured pressure. In another example, the physiological data generator P1 is composed of an electrode in an electrocardiograph, wherein it is operable to measure a cardiac action potential, and the signal processing unit is operable to generate an electrocardiogram from the measured action potential. In yet another example, the physiological data generator P1 is composed of an electrode in an electromyograph, wherein it is operable to measure a muscular action potential, and the signal processing unit is operable to generate an electromyogram from the measured action potential. In still another example, the physiological data generator P1 is composed of a probe unit in a pulse oxymeter, wherein the probe unit is operable to emit an infrared light beam and a red light beam to a subject and generate photoelectric pulse wave data based on respective light amounts of resulting reflected infrared and read light beams (or respective light amounts of resulting transmitted infrared and read light beams), and the signal processing unit is operable to obtain a blood oxygen level and a heart rate from the photoelectric pulse wave data. In this embodiment, the physiological data generator P1 is composed, for example, of a microwave Doppler sensor configured to generate Doppler shift data of Doppler-shifted reflected microwave obtained by emitting a microwave to a subject, in order to measure a body motion or a respiratory rate of the subject, and the signal processing unit is operable to obtain a body motion or a respiratory rate from the measured Doppler shift data. Such a microwave Doppler sensor is e.g. disclosed in JP2012-75861A and JP2012-97670A. Such a microwave Doppler sensor is used when the subject monitoring apparatus MD determines a body state of a subject, based on image data of the subject and Doppler shift data representing a microwave reflected by the subject, as described later, so that the subjects body state can be determined in a non-contact manner.

Figure 7:
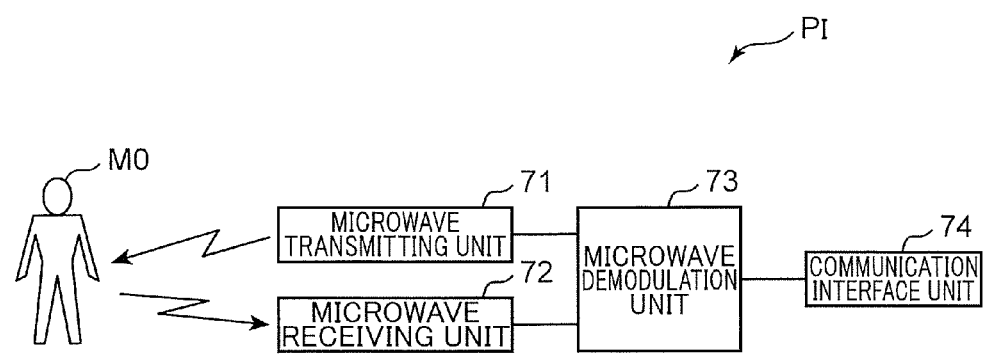
FIG. 7 is a diagram depicting a configuration of a physiological data generator in the subject monitoring system depicted in FIG. 1.

More specifically, for example, as depicted in FIG. 7 the physiological data generator P1 equipped with a microwave Doppler sensor includes: a microwave transmitting unit 71 configured to emitting a microwave to a subject; a microwave receiving unit 72 configured to receive a reflected microwave reflected by the subject; a microwave demodulation unit 73 connected to each of the microwave transmitting unit 71 and the microwave receiving unit 72 and configured to generate Doppler shift data based on the microwave emitted from the microwave transmitting unit 71 and the reflected microwave received by microwave receiving unit 72; and a communication interface unit 74 connected to the microwave demodulation unit 73. The microwave transmitting unit 71 is disposed such that an emission direction thereof is coincident with a direction allowing the microwave transmitting unit 71 to appropriately emit a microwave to a space in which the subject is usually present, and the microwave receiving unit 72 is disposed to be allowed to receive a reflected wave of the microwave emitted from the microwave transmitting unit 71 to the space. As with the communication IF unit 64, the communication interface unit 74 is an interface for sending and receiving a communication signal with respect to the subject monitoring apparatus MD therethrough via the communication network NW. In this physiological data generator P1, a microwave is emitted from the microwave transmitting unit 71 to the space and thereby emitted onto a subject MO, whereafter a part of the microwave is reflected by a body surface of the subject MO, and a part of the remaining microwave entering into the subject is reflected by respiratory muscles. A microwave reflected by the subject MO (reflected microwave) is received by the microwave receiving unit 72. Then, through the microwave demodulation unit 73, Doppler shift data is demodulated based on the microwave in the microwave transmitting unit 71 and the reflected microwave in the microwave receiving unit 72. This Doppler shift data is superimposed on a communication signal, and transmitted as subject's physiological data to the subject monitoring apparatus MD through the communication interface unit 74. In this case, a Doppler shift corresponding to a body motion and a movement of the respiratory muscles of the subject occurs in the reflected microwave, so that the Doppler shift data corresponds to the body motion and the movement of the respiratory muscles of the subject. Thus, the body motion and the respiratory rate of the subject can be obtained by subjecting the Doppler data to information processing, as described later. In addition, the heart rate can be obtained from the Doppler shift data.

Returning to FIG. 1, the subject monitoring apparatus MD is configured to monitor a subject, and determine a body state of the subject, based on the subject's image data received from the image data generator MC and the subject's physiological data received from the physiological data generator P1, wherein the subject monitoring apparatus MD is operable, when it is determined that the subject's body state is abnormal, to issue a notification indicating that the subject is in an abnormal state, to an associated one of the communication terminals CT. The abnormal state is an event which occurs in the subject's body and is deemed to require prompt help for the subject by others, and is preliminarily appropriately set depending on a type of subject. By referring to the communication terminal CT, a watcher can recognize that the subject is determined to be in the abnormal state. In this embodiment, the image data and the physiological data are received, respectively, from the image data generator MC and the physiological data generator P1 via the communication network NW, and, for this purpose, the subject monitoring apparatus MD has a communication function. For example, this the subject monitoring apparatus MD includes a communication IF unit 1, an input unit 2, an output unit 3, a processing controller 4, and a storage unit 5, as depicted in FIG. 2.

The communication IF unit 1 is an interface connected to the processing controller 4 and configured to send and receive a communication signal with respect to the image data generator MC and with respect to the physiological data generator P1 therethrough, via the communication network NW. The subject's image data transmitted from the image data generator MC and received through the communication IF unit 1 is output from the communication IF unit 1 to the processing controller 4, and the subject's physiological data transmitted from the physiological data generator P1 and received through the communication IF unit 1 is output from the communication IF unit 1 to the processing controller 4. As above, in this embodiment, the subject's image data generated from the image data generator MC is input into the subject monitoring apparatus MD through the communication IF unit 1. Thus, the communication IF unit 1 can be regarded as one example of an image data input unit. On the other hand, the subject's physiological data generated from the physiological data generator P1 is input into the subject monitoring apparatus MD through the communication IF unit 1. Thus, the communication IF unit 1 can also be regarded as one example of a physiological data input unit.

In this embodiment, the subject monitoring apparatus MD, the image data generator MC and the physiological data generator P1 are connected via the communication network NW in a mutually communicable manner. Alternatively, the subject monitoring apparatus MD and the image data generator MC may be connected together via a dedicated distribution cable. In this case, an interface circuit for interfacing data input and output with respect to the image data generator MC can be regarded as one example of the image data input unit. Further, the subject monitoring apparatus MD and the physiological data generator P1 may be connected together via a dedicated distribution cable. In this case, an interface circuit for interfacing data input and output with respect to the physiological data generator P1 can be regarded as one example of the physiological data input unit. Examples of the interface circuit include an RS-232 interface circuit using a serial communication method, and an interface circuit compliant with the USB (Universal Serial Bus) standard. In the case where the processing controller 4 can handle the subject's image data generated from the image data generator MC, without intervention of such an interface circuit, a terminal for connecting the distribution cable can be regarded as one example of the image data input unit. Further, in the case where the processing controller 4 can handle the subject's physiological data generated from the physiological data generator PI, without intervention of such an interface circuit, a terminal for connecting the distribution cable can be regarded as one example of the physiological data input unit.

The input unit 2 is a device connected to the processing controller 4 and configured to input, into the subject monitoring apparatus MD, various commands such as a command to start monitoring, an identifier of each subject, various data required for monitoring a subject, such as abnormality data representing abnormal states for use in determination as to whether or not a body state is abnormal, and others. For example, it may be a keyboard or a mouse. The output unit 3 is a device connected to the processing controller 4 and configured to output a commend and data input from the input unit 2, and subject's image and subject's body state determined by the subject monitoring apparatus MD. For example, it may be a display device such as a CRT display device, a LCD device or an organic EL display device, or a printing device such as a printer.

The input unit 2 and the output unit 3 may be constructed as a touch panel. In case of constructing such a touch panel, for example, the input unit 2 is a certain type (e.g., resistive or capacitive type) of position input device configured to detect and input an operated position, and the output unit 3 is a display device. The touch panel is constructed such that the position input device is provided on a display surface of the display device, wherein, when one or more imputable candidate items are displayed on the display device, and a user touches a display position where a desired one of the items is displayed, the touched position is detected by the position input device, and the item displayed at the detected position is input into the subject monitoring apparatus MD as an input item operated by the user. In such a touch panel, a user can intuitively understand an input operation, so that it becomes possible to provide a subject monitoring apparatus MD which is easy to handle by a user.

The storage unit 5 includes: a non-volatile storage element such as ROM (Read Only memory) or EEPROM (Electronically Erasable Programmable Read Only Memory) preliminarily storing therein various programs to be executed by the processing controller 4 e.g., a subject monitoring program for monitoring a subject, data required for executing the programs, and others; a volatile storage element such as RAM (Random Access Memory) serving as a so-called working memory of the processing controller 4; and a peripheral circuit thereof. The storage unit 5 may comprise a storage device such as a hard disk device having a relatively-large capacity. The storage unit 5 functionally comprises: an image data storage section 51 for storing therein subject's image data on a per-aftermentioned subject identifier basis; a posture record storage section 52 for storing therein a record about subject's posture; a falling record storage section 53 for storing a record about subject's falling; a location record storage section 54 for storing a record about subject's location; and a physiological data storage section 55 for storing therein subject's physiological data on a per-aftermentioned subject identifier basis.

More specifically, the posture record storage section 52 is configured to store therein a subject identifier for specifying and identifying a subject, a posture determination clock time when a posture of the subject is determined, and the posture of the subject, in associated relation with each other, e.g., in the form of a table. For example, a posture recode table for registering therein a record about subjects posture has: a subject identifier field for registering therein a subject identifier of a subject; a posture determination clock time field for registering therein a posture determination clock time when a posture of the subject corresponding to the subject identifier registered in the subject identifier field is determined; and a posture field for registering therein the posture of the subject corresponding to the subject identifier registered in the subject identifier field, wherein a record is created on a per-subject identifier basis and on a per-posture determination clock time. Similarly, a falling recode storage section 53 is configured to store therein a subject identifier of a subject, a falling determination clock time when falling of the subject is determined, and the presence or absence of falling of the subject, in associated relation with each other, e.g., in the form of a table. For example, a falling recode table for registering therein a record about subject's falling has: a subject identifier field for registering therein a subject identifier of a subject; a falling determination clock time field for registering therein a falling determination clock time when falling of the subject corresponding to the subject identifier registered in the subject identifier field is determined; and a falling field for registering therein the presence or absence of falling of the subject corresponding to the subject identifier registered in the subject identifier field, wherein a record is created on a per-subject identifier basis and on a per-falling determination clock time. Similarly, a location recode storage section 54 is configured to store therein a subject identifier of a subject, a location determination clock time when a location of the subject is determined, and the location of the subject, in associated relation with each other, e.g., in the form of a table. For example, a location recode table for registering therein a record about subject's location has: a subject identifier field for registering therein a subject identifier of a subject; a location determination clock time field for registering therein a location determination clock time when a location of the subject corresponding to the subject identifier registered in the subject identifier field is determined; and a location field for registering therein the location of the subject corresponding to the subject identifier registered in the subject identifier field, wherein a record is created on a per-subject identifier basis and on a per-location determination clock time.

In the image data storage section 51, the posture record storage section 52, the falling record storage section 53, the location record storage section 54 and the physiological data storage section 55, in place of or in addition to the subject identifier, an image data generator identifier for specifying and identifying the image data generator MC may be used. Similarly, in place of or in addition to the subject identifier, a physiological data generator identifier for specifying and identifying the physiological data generator P1 may be used. In this case, each of a correspondence relationship between the subject identifier and the image data generator identifier, and a correspondence relationship between the subject identifier and the physiological data generator identifier is preliminarily set and stored. As described later, the processing controller 4 is configured to determine a first body state of a subject by using the posture, location and falling records of the subject stored in the storage unit 5. Each of the posture record storage section 52, the falling record storage section 53 and the location record storage section 54 in the storage unit 5 may have a storage capacity capable of storing respective records for a period of time of last several seconds.

The processing controller 4 is configured to control respective units or sections of the subject monitoring apparatus MD depending on their functions to thereby govern the entire control of the subject monitoring apparatus MD. The processing controller 4 may also be configured to control an imaging direction and an angle of field of the image data generator MC via the communication IF unit 1 and the communication network NW. The processing controller 4 is operable, based on image data of a subject received from the image data generator MC, and physiological data of the subject received from the physiological data generator P1, to determine a body state of the subject, and, when it is determined that the body state of the subject is abnormal, to issue a notification indicating that the subject is in an abnormal state, to an associated one of the communication terminals CT.

For example, this processing controller 4 comprises a CPU (Central Processing Unit) and a peripheral circuit thereof. During execution of a program, a control unit 41, a first body state determination unit 42, a second body state determination unit 43, and a notification control unit 44 are functionally formed in the processing controller 4.

The control unit 41 serves as means to control respective units and sections of the subject monitoring apparatus MD depending on their functions so as to monitor a subject. The control unit 41 is operable, in response to receiving image data from the image data generator MC via the communication IF unit 1, to store the received image data in the image data storage section 51 in associated relation with a relevant subject identifier, and, in response to receiving physiological data from the physiological data generator PI via the communication IF unit 1, to store the received physiological data in the physiological data storage section 55 in associated relation with a relevant subject identifier.

The first body state determination unit 42 serves as means to, based on image data of a subject input from the image data generator MC via the communication network NW, determine a first body state of the subject. The first body state determination unit 42 may acquire the image data from the image data storage section 51 or from the control unit 41 when it receives the image data. The first body state of the subject is a motion of the subject determined based on the image data of the subject by using a heretofore-known motion analysis algorithm for analyzing a motion, and examples of the first body state include: a sitting-up motion arising when the subject sits up on a bed; a leaving motion arising when the subject leaves from the bed; a fall-off motion arising when the subject falls off from the bed; and a fall-over motion arising when the subject falls over. As the motion analysis algorithm, it is possible to use heretofore-known image processing programs, motion analysis programs, object tracking programs and pattern recognition programs published in so-called "OpenCV (Open Source Computer Vision Library). More specifically, as depicted in FIG. 3, the first body state determination unit 42 includes a person region extraction section 421, a posture detection section 422, a falling detection section 423, a location detection section 424, and a first determination section 425.

The person region extraction section 421 serves as means to import image data of a subject and extract a person region from an image in the imported image data of the subject. The person region means a region in which a person's image is shown up. More specifically, in one example, the person region extraction section 421 is operable to extract a candidate region for the person region, from a difference image between an image and a background image in the imported image data of the subject. In another example, the person region extraction section 421 is operable to subject an image in the imported image data of the subject to moving body detection to thereby extract a candidate region for the person region. Then, the person region extraction section 421 is operable to determine whether or not a size of the extracted candidate region is equal to or greater than a person region determination threshold. The person region determination threshold is preliminarily and appropriately set depending on a size of a person region in an image obtained when an actual person is imaged, considering a magnification ratio of the imaging optical system 61 of the image data generator MC, and others. As a result, when it is determined that the size of the candidate region is equal to or greater than the person region determination threshold, the person region extraction section 421 is operable to recognize the candidate region as the person region. On the other hand, when it is determined that the size of the candidate region is less than the person region determination threshold, the person region extraction section 421 is operable to recognize the candidate region as noise. After extracting the person region in this way, the person region extraction section 421 is operable to output the extracted person region to each of the posture detection section 422, the falling detection section 423 and the location detection section 424.

The posture detection section 422 serves as means to, based on the person region input from the person region extraction section 421, detect a posture of the subject. More specifically, the posture detection section 422 is operable to approximate a contour of the person region input from the person region extraction section 421 by a rectangular or elliptical shape, and determine a posture of the subject based on a horizontal direction in the approximated contour of the person region, a vertical direction perpendicular to the horizontal direction, and a vertical-to-horizontal ratio (=(vertical length)/(horizontal length)). For example, assuming that a position and an imaging direction of the image data generator MC, and a position and a direction of a bed used by the subject are known, the posture of the subject can be determined in the following manner. In one example, when the vertical length is greater than the horizontal length, and the vertical-to-horizontal ratio is equal to or greater than a preliminarily-set first posture determination threshold, it is determined that the subject is in a standing posture. In another example, when the vertical length is less than the horizontal length, and the vertical-to-horizontal ratio is less than the first posture determination threshold, it is determined that the subject is in a lying posture. In yet another example, when the vertical length is approximately equal to the horizontal length, i.e., the vertical-to-horizontal ratio is approximately one, and the vertical length (or the horizontal length) is equal to or greater than a preliminarily-set second posture determination threshold, it is determined that the subject is in a sitting posture (sitting-up posture). In still another example, when the vertical length is approximately equal to the horizontal length, i.e., the vertical-to-horizontal ratio is approximately one, and the vertical length (or the horizontal length) is less than the second posture determination threshold, it is determined that the subject is in a squatting posture. Each of the first and second posture determination thresholds may be preliminarily set to an appropriate value by measuring a plurality of samples and subjecting obtained measurement results to statistical processing. After detecting the posture of the subject in this way, the posture detection section 422 is operable to store the detected posture of the subject in the posture record storage section 52 in associated relation with a relevant subject identifier (or image data generator identifier) and a relevant posture determination clock time, and output the detected posture of the subject to the first determination section 425 in associated relation with the relevant subject identifier (or image data generator identifier) and the relevant posture determination clock time.

The falling detection section 423 serves as means to, based on the person region input from the person region extraction section 421, detect falling of the subject. More specifically, assuming that intervals of generation of image data by the image data generator MC (e.g., frame rate) is known, the falling detection section 423 is operable to calculate a moving direction and a moving speed of the person region, based on a position of the person region input this time from the person region extraction section 421, and a position of the person region input last time from the person region extraction section 421, wherein the falling detection section 423 is operable, when the moving direction of the person region is downward, and the moving speed of the person region is approximately equal to a free-fall speed, to determine that the subject falls off, and, when at least one of the moving direction and the moving speed of the person region does not satisfy the above condition, to determine that the subject has not fallen off. In the above example, the moving direction and moving speed are determined based on the newest position of the person region and the last position of the person region. Alternatively, the moving direction and moving speed may be determined based on the newest position of the person region and one or more previous positions (e.g., the last position and the position before last) of the person region. After detecting the presence or absence of falling of the subject in this way, the falling detection section 423 is operable to store the detected presence or absence of falling of the subject in the falling record storage section 53 in associated relation with a relevant subject identifier (or image data generator identifier) and a relevant falling determination clock time, and output the detected presence or absence of falling of the subject to the first determination section 425 in associated relation with the relevant subject identifier (or image data generator identifier) and the relevant falling determination clock time.

The location detection section 424 serves as means to, based on the person region input from the person region extraction section 421, detect a location of the subject. More specifically, assuming that a position and the position and a size of the bed used by the subject is known, the location detection section 424 is operable to determine whether or not the person region input from the person region extraction section 421 is located on a bed region, to thereby determine a location of the subject. The bed region means a region in which a bed's image is shown up. The location detection section 424 is operable, when the person region is located on the bed region, to recognize that the subject is located on the bed, and, when the person region is located on a boundary of the bed region, to recognize that the subject sits on an edge of the bed while extending his/her feet downwardly from the bed. The location detection section 424 is also operable, when the person region is not located on the bed region, to recognize that the subject is located at a position away from the bed (out-of-bed location). After detecting the location of the subject in this way, the location detection section 424 is operable to store the detected location of the subject in the location record storage section 54 in associated relation with the relevant subject identifier (or image data generator identifier) and a relevant location determination clock time, and output the detected location of the subject to the first determination section 425 in associated relation with the relevant subject identifier (or image data generator identifier) and the relevant location determination clock time.

The first determination section 425 serves as means to, based on the posture of the subject detected by the posture detection section 422, the presence or absence of falling of the subject detected by the falling detection section 423, and the location of the subject detected by the location detection section 424, determine the first body state of the subject. More specifically, the first determination section 425 is operable to determine, as the first body state of the subject, one of "sitting-up", "out-of-bed", "fall-off", "fall-over" and "no-event", based on records of the posture, the presence or absence of falling, and the location of the subject. For example, the first determination section 425 is operable, based on: the posture of the subject detected this time by the posture detection section 422, the presence or absence of falling of the subject detected this time by the falling detection section 423, and the location of the subject detected this time by the location detection section 424; and the posture of the subject detected last time by the posture detection section 422, the presence or absence of falling of the subject detected last time by the falling detection section 423, and the location of the subject detected last time by the location detection section 424, each stored in the posture record storage section 52, the falling record storage section 53 and the location record storage section 54 of the storage unit 5, to determine, as the first body state of the subject, one of "sitting-up", "out-of-bed", "fall-off", "fall-over" and "no-event". Then, the first determination section 425 is operable, when the determination is made as "fall-off", to determine that the subject is in an abnormal state, and, when the determination is made as "fall-over", to determine that the subject is in the abnormal state. On the other hand, in this embodiment, the first determination section 425 is operable, in any case other than the above, to determine that the subject is not in the abnormal state. After determining the first body state of the subject, the first determination section 425 is operable to output a result of the determination (in this embodiment, one of "sitting-up", "out-of-bed", "fall-off", "fall-over" and "no-event", and the presence or absence of the abnormal state of the subject) to the notification control unit 44.

The second body state determination unit 43 serves as means to, based on physiological data of the subject input from the physiological data generator P1 via the communication network NW, determine a second body state of the subject. The second body state determination unit 43 may acquire the physiological data from the physiological data storage section 55 or from the control unit 41 when it receives the physiological data. The second body state of the subject is physiological information of the subject determined based on the physiological data of the subject by using a heretofore-known analysis algorithm. For example, in this embodiment, the second body state is the number of body motions (body motion number) and a respiratory rate obtained from Doppler shift data. An analysis algorithm for obtaining a body motion number and a respiratory rate from Doppler shift data is described, for example, in JP 2012-75861A and JP 2012-97670A. More specifically, as depicted in FIG. 4, the second body state determination unit 43 comprises a differential processing section 431, a body motion detection section 432, a fast Fourier transformation (hereinafter abbreviated as "FFT") section 433, a respiration detection section 434, and a second determination section 435.

The differential processing section 431 serves as means to import Doppler shift data as the physiological data of the subject, and differentiate the imported Doppler shift data of the subject. The differential processing section 431 is operable to the differentiated Doppler shift data to the body motion detection section 432. The body motion detection section 432 serves as means to detect the body motion number of the subject based on the differentiated Doppler shift data. More specifically, the body motion detection section 432 is operable to count the number of body motions on an assumption that one body motion occurs when the differentiated Doppler shift data is equal to or greater than a preliminarily-set + body motion determination threshold, and one body motion occurs when the differentiated Doppler shift data is equal to or less than a preliminarily-set − body motion determination threshold, and calculate the number of counted body motions per unit time, as the body motion number. The body motion means a motion of a subject, except for a respiratory motion. Each of the + body motion determination threshold and the − body motion determination threshold is preliminarily set to an appropriate value by measuring a plurality of samples and subjecting obtained measurement results to statistical processing. After obtaining the body motion number, the body motion detection section 432 is operable to output the obtained body motion number to the second determination section 435.

The FFT section 433 serves as means to import the Doppler shift data as the physiological data of the subject to accumulate the physiological data of the subject for a given period of time, and then subjecting the accumulated physiological data to fast Fourier transformation to obtain a frequency distribution of the Doppler shift data. The FFT section 433 is operable to output the obtained frequency distribution of the Doppler shift data to the respiration detection section 434. The respiration detection section 434 serves as means to detect the respiratory rate of the subject based on the frequency distribution of the Doppler shift data. More specifically, the respiration detection section 434 is operable to detect, as a respiratory fundamental component, a frequency component having a highest intensity (peak frequency component) in the frequency distribution of the Doppler shift data, and multiply the respiratory fundamental component by 60 to obtain the respiratory rate per unit time. After obtaining the respiratory rate, the respiration detection section 434 is operable to output the obtained respiratory rate to the second determination section 435.

The second determination section 435 serves as means to, based on the body motion number of the subject detected by the body motion detection section 432 and the respiratory rate of the subject detected by the respiration detection section 434, determine the second body state of the subject. More specifically, the second determination section 435 is operable, when it is determined, based on the respiratory rate of the subject, that the subject is in an apneic state (state in which the respiratory rate is 0 or significantly small, e.g., two or three), and it is determined, based on the body motion number of the subject, that there was a body motion, to determine that the subject is in the abnormal state, and, when it is determined, based on the respiratory rate of the subject, that the subject is in a relatively-rapid respiration state (state in which the respiratory rate is equal to or greater than a preliminarily-set respiratory abnormality threshold), and it is determined, based on the body motion number of the subject, that there was a body motion, to determine that the subject is in the abnormal state. On the other hand, in this embodiment, the second determination section 435 is operable, in any case other than the above, to determine that the subject is not in the abnormal state. The respiratory abnormality threshold may be preliminarily set to an appropriate value by measuring a plurality of samples and subjecting obtained measurement results to statistical processing, while taking into account medical viewpoints. After determining the second body state of the subject, the second determination section 435 is operable to output a result of the determination (in this embodiment, the body motion number, the respiratory number and the presence or absence of the abnormal state of the subject) to the notification control unit 44.

The notification control unit 44 serves as means to, when each of the first and second body states of the subject determined by respective ones of the first and second body state determination units 42, 43 is an abnormal state, to issue a notification indicating that the subject is in an abnormal state, and, when one of the first and second body states of the subject, determined by a corresponding one of the first and second body state determination units 42, 43 is not an abnormal state, to cause the one of the first and second body state determination units 42, 43 to re-perform the determination, and then determine whether or not the subject's abnormal state-indicating notification should be issued, based on a result of the determination about the one of the first and second body states of the subject, re-performed by the one of the first and second body state determination units 42, 43.

More specifically, in this embodiment, the notification control unit 44 is operable, in response to ascertaining a situation where the body state of the subject determined by one of the first and second body state determination units 42, 43 is a given first abnormal state, and the body state of the subject determined by a remaining one of the first and second body state determination units 42, 43 is a second abnormal state corresponding to the first abnormal state, as the situation where each of the first and second body states of the subject determined by respective one of the first and second body state determination units 42, 43 is an abnormal state, to issue the subject's abnormal state-indicating notification. In this embodiment, the notification control unit 44 is operable, in response to recognizing a situation where the body state of the subject determined by one of the first and second body state determination units 42, 43 is the first abnormal state, and the body state of the subject determined by a remaining one of the first and second body state determination units 42, 43 is not the second abnormal state corresponding to the first abnormal state, as the situation where one of the first and second body states of the subject, determined by a corresponding one of the first and second body state determination units 42, 43 is not an abnormal state, to cause the remaining one of the first and second body state determination units 42, 43 to re-perform the determination about the corresponding body state of the subject, for a given period of time or by a given number of times, and then determine whether or not the subject's abnormal state-indicating notification should be issued, wherein the notification control unit 44 is operable, when the corresponding body state of the subject is determined to be the second abnormal state, within the given period of time or the given number of times, to issue the subject's abnormal state-indicating notification.

In this embodiment, the first body state determination unit 42 is operable, based on the image data of the subject, to further detect a location of the subject, wherein the notification control unit 44 is operable, during the determination as to whether or not the subject's abnormal state-indicating notification should be issued, to re-determine the second body state of the subject determined by the second body state determination unit 43, based on the location of the subject detected by the first body state determination unit 42.

In this embodiment, the subject monitoring apparatus MD is equipped with a mailer, wherein the notification control unit 44 is operable to issue the subject's abnormal state-indicating notification to a relevant watcher via e-mail. In this e-mail, a message indicating that the subject is in the abnormal state is described. In addition to or in place of the message, a link (URL) for referring to the image of the subject in a streaming manner may be set in the e-mail.

In this embodiment, the subject monitoring apparatus MD is configured to issue the subjects abnormal state-indicating notification to a relevant watcher via e-mail, and, for this purpose, the subject monitoring system MS includes a non-depicted mail server which is a server computer for delivering e-mails. The subject monitoring apparatus MD may additionally function as the mail server. In this case, the storage unit 5 further includes an e-mail storage section 57 indicated by the broken line in FIG. 2, which is configured to store therein e-mails on a per-user (per-mail address) basis, and the processing controller 4 further includes an e-mail delivery unit 46 indicated by the broken line in FIG. 2, which is configured to delivery e-mails, for example, using POP (Post Office Protocol) and SMTP (Simple Mail Transfer Protocol). The image of the subject may be directly delivered by the image data generator MC or may be delivered by a non-depicted image server. The image server is a server computer configured to receive and store the image of the subject from the image data generator MC, and, in response to a request from a client terminal, deliver the image data of the subject. The subject monitoring apparatus MD may additionally function as the image server. In this case, the processing controller 4 further includes the image data delivery unit 47 indicated by the broken line in FIG. 2, which is configured to deliver the image data of the subject stored in the image data storage section 51 of the storage unit 5 on a per-subject identifier (per-image data generator identifier) basis, using a given protocol.

More specifically, for example, as depicted in FIG. 5, the notification control unit 44 comprises a first ascertainment section 441, a second ascertainment section 442, and a notification section 443.

The first ascertainment section 441 is operable, based on the respective determination results input from the first and second determination sections 425, 435 of the first and second body state determination units 42, 43, to ascertain whether or not the first body state of the subject is a preliminarily-set abnormal state A, and ascertain whether or not the second body state of the subject is a preliminarily-set abnormal state B corresponding to the abnormal state A, in order to determine whether or not the subject's abnormal state-indicating notification should be issued. The first ascertainment section 441 is operable, when the first body state of the subject determined by the first body state determination unit 42 is the abnormal state A, and the second body state of the subject determined by the second body state determination unit 43 is the abnormal state B, to output information indicating that the subject is in the abnormal state, to the notification section 443. The first ascertainment section 441 is operable, when the first body state of the subject determined by the first body state determination unit 42 is not the abnormal state A, and the second body state of the subject determined by the second body state determination unit 43 is the abnormal state B, to cause the first body state determination unit 42 to re-perform the determination about the first body state of the subject, thereby determining whether or not the subject's abnormal state-indicating notification should be issued, wherein the first ascertainment section 441 is operable, when the first body state of the subject is determined to be the abnormal state A, within the given period of time or the given number of times, to output the information indicating that the subject is in the abnormal state, to the notification section 443.

The second ascertainment section 442 is operable, based on the respective determination results input from the first and second determination sections 425, 435 of the first and second body state determination units 42, 43, to ascertain whether or not the second body state of the subject is a preliminarily-set abnormal state C, and ascertain whether or not the first body state of the subject is a preliminarily-set abnormal state D corresponding to the abnormal state C, in order to determine whether or not the subject's abnormal state-indicating notification should be issued. The second ascertainment section 442 is operable, when the second body state of the subject determined by the second body state determination unit 43 is the abnormal state C, and the first body state of the subject determined by the first body state determination unit 42 is the abnormal state D, to output information indicating that the subject is in the abnormal state, to the notification section 443. The first ascertainment section 441 is operable, when the second body state of the subject determined by the second body state determination unit 43 is not the abnormal state C, and the first body state of the subject determined by the first body state determination unit 42 is the abnormal state D, to cause the second body state determination unit 43 to re-perform the determination about the second body state of the subject, thereby determining whether or not the subject's abnormal state-indicating notification should be issued, wherein the second ascertainment section 442 is operable, when the second body state of the subject is determined to be the abnormal state C, within the given period of time or the given number of times, to output the information indicating that the subject is in the abnormal state, to the notification section 443.

The second ascertainment section 442 is operable, during the determination as to whether or not the subject's abnormal state-indicating notification should be issued, to further determine (re-determine) the second body state of the subject determined by the second body state determination unit 43, based on the location of the subject detected by the first body state determination unit 42.

In this embodiment configured as above, when the body state of the subject determined by one of the first and second determination sections 425, 435 is not an abnormal state, the subject's abnormal state-indicating notification is kept on hold, and one of the image data-based determination and the physiological data-based determination, corresponding to the one of the first and second determination sections 425, 435, is successively performed for the given period of time or by the given number of times.

The notification section 443 is operable, in response to receiving the subject's abnormal state-indicating information from both of the first and second ascertainment sections 441, 442, to issue the subject's abnormal state-indicating notification to a relevant watcher via e-mail. The notification section 443 may be configured to describe, in an e-mail, a link (URL) for referring to the image of the subject in a streaming manner, in addition to or in place of a message indicating that the subject is in the abnormal state, as mentioned above.

Further, the notification section 443 may be configured to, when issuing the subject's abnormal state-indicating notification to a relevant watcher via e-mail, to describe, in the above e-mail, at least one of the first body state (in this embodiment, "sitting-up", "out-of-bed", "fall-off", "fall-over") of the subject determined by the first body state determination unit 42 and the second body state (in this embodiment, the body motion number, the respiratory rate) of the subject determined by the second body state determination unit 43, in addition to information indicating that the subject is in the abnormal state.

The communication IF unit 1, the input unit 2, the output unit 3, the processing controller 4 and the storage unit 5 may be composed, for example, of a computer, more specifically, a notebook-size or desktop personal computer.

Figure 8:
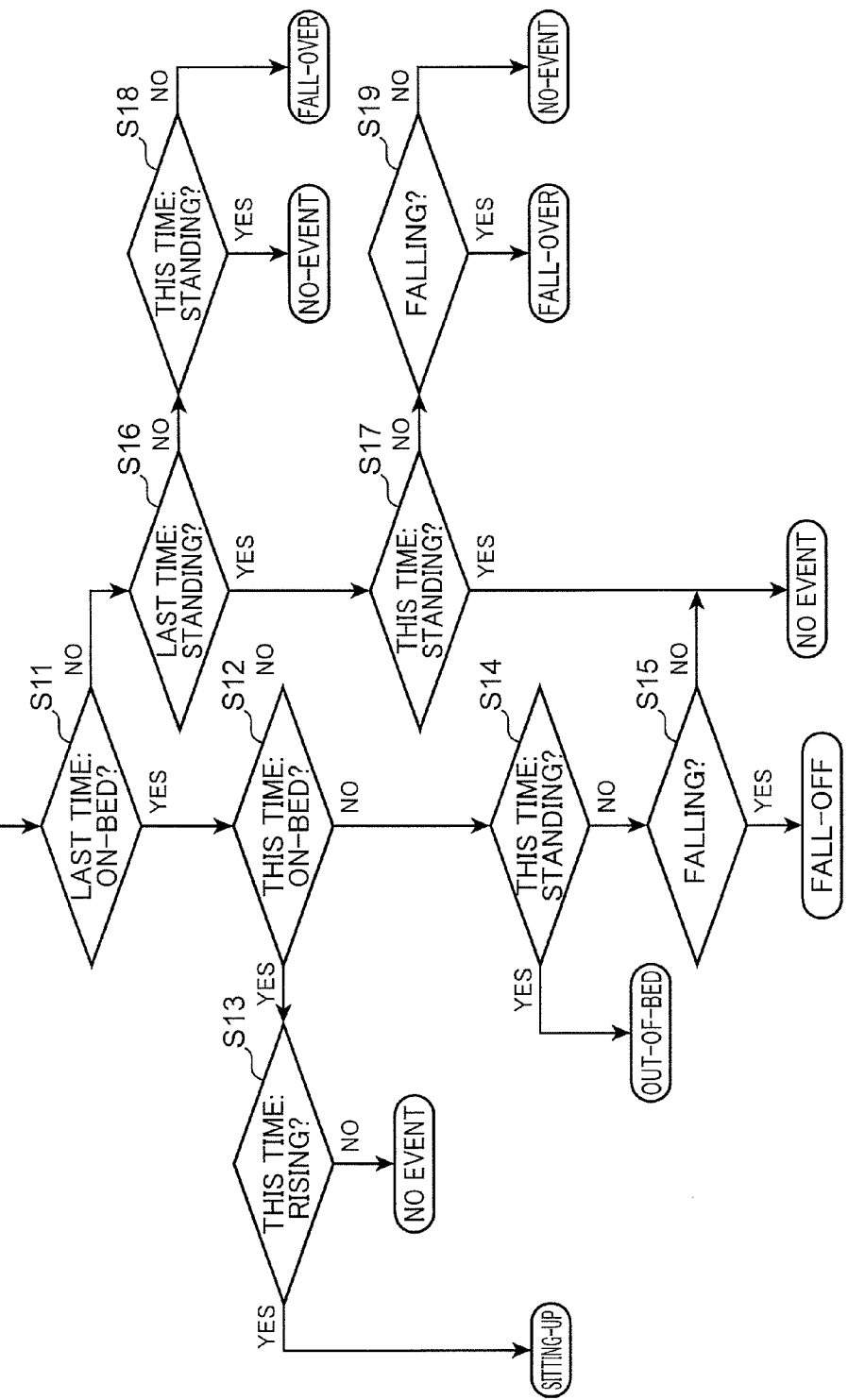
FIG. 8 is a flowchart depicting an operation of the first body state determination unit depicted in FIG. 3.

Next, an operation of this embodiment will be described. FIG. 8 is a flowchart depicting an operation of the first body state determination unit depicted in FIG. 3. FIG. 9 is a flowchart depicting an operation of the subject monitoring system in FIG. 1.

Upon accepting an activation command, for example, from the input unit 2 according to a manual operation of a user, the subject monitoring apparatus MD executes a subject monitoring program. During the execution of the subject monitoring program, the control unit 41, the first body state determination unit 42, the second body state determination unit 43 and the notification control unit 44 are functionally formed in the processing controller 4.

Then, upon starting the monitoring, the subject monitoring apparatus MD sequentially imports image data from the image data generator MC at first time intervals of a given period of time via the communication network NW, and sequentially imports physiological data from the physiological data generator PI at second time intervals of a given period of time via the communication network NW. The first time interval is a period of time required for allowing the first body state determination unit 42 to determine "fall-off", and may be preliminarily set in an appropriate manner. For example, the first time interval may be any period of time falling within the range of 0.1 to 0.3 sec. On the other hand, the image data generator MC may be configured to generate and transmit the image data to the subject monitoring apparatus MD, at intervals of a period of time less than the above given period of time (e.g., 24 fps, 30 fps or 60 fps). In this case, the subject monitoring apparatus MD may be configured to appropriately cull a part of a plurality of pieces of image data and use the remaining pieces of image data. From a viewpoint of reducing a communication capacity and communication traffic in the communication network NW, the first time interval is preferably set to any period of time falling within the range of 0.1 to 0.3 sec, as in this embodiment. The second time interval is a period of time required for allowing the second body state determination unit 43 to determine the body motion number or the respiratory rate, and may be preliminarily set in an appropriate manner.

In a situation where image data of a subject is sequentially imported at the first time intervals, the first body state determination unit 42 of the processing controller 4 of the subject monitoring apparatus MD determines the first body state of the subject, based on the image data of the subject input from the image data input unit MC via the communication network NW.

More specifically, the person region extraction section 421 of the first body state determination unit 42 extracts a person region from an image of the image data of the subject, and outputs the extracted person region to each of the posture detection section 422, the falling detection section 423 and the location detection section 424, as mentioned above. Then, the posture detection section 422, the falling detection section 423 and the location detection section 424 detect, respectively, a posture of the subject, the presence or absence of falling of the subject, and a location of the subject, based on the person region input from the person region extraction section 421, as mentioned above. Then, each of the posture detection section 422, the falling detection section 423 and the location detection section 424 stores a result of the detection in a corresponding one of the posture record storage section 52, the falling record storage section 53 and the location record storage section 54, in associated relation with a relevant subject identifier (or image data generator identifier) and a relevant determination clock time, and outputs the detection result to the first determination section 425 in associated relation with the relevant subject identifier (or image data generator identifier) and the relevant determination clock time.

Then, the first determination section 425 determines the first body state of the subject, based on the posture, the presence or absence of falling, and the location of the subject detected, respectively, by the detection sections 422, 423, 424. More specifically, as depicted in FIG. 8, first of all, the first determination section 425 determines whether or not a last location of the subject determined last time and stored in the location record storage section 54 lies on a bed (S11). As a result, when it is determined that the last location of the subject lies on the bed (Yes), the first determination section 425 performs processing S12. On the other hand, when it is determined that the last location of the subject does not lie on the bed (No), the first determination section 425 performs processing S16.

In the processing S12, the first determination section 425 determines whether or not a latest location of the subject input this time from the location detection section 424 lies on the bed (S12). As a result, when it is determined that the latest location of the subject lies on the bed (Yes), the first determination section 425 performs processing S13. On the other hand, when it is determined that the latest location of the subject does not lies on the bed (No), the first determination section 425 performs processing S14.

In the processing S13, the first determination section 425 determines whether or not a latest posture of the subject input this time from the posture detection section 422 is a sitting posture (where the subject rises and sits) (S13). As a result, when it is determined that the latest posture of the subject is the sitting posture (Yes), the first determination section 425 determines that the first body state of the subject is "sitting-up". On the other hand, when it is determined that the latest posture of the subject is not the sitting posture (No), the first determination section 425 determines that there is no event (non-detection).

In the processing S14, the first determination section 425 determines whether or not the latest posture of the subject input this time from the posture detection section 422 is a standing posture (S14). As a result, when it is determined that the latest posture of the subject is the standing posture (Yes), the first determination section 425 determines that the first body state of the subject is "out-of-bed". On the other hand, when it is determined that the latest posture of the subject is not the standing posture (No), the first determination section 425 performs processing S15.

In the processing S15, the first determination section 425 determines whether or not a latest detection result (falling of the subject) input this time from the falling detection section 423 is the presence of falling (S15). As a result, when it is determined that the latest posture of the subject is the presence of falling (Yes), the first determination section 425 determines that the first body state of the subject is "fall-off". On the other hand, when it is determined that the latest posture of the subject is the absence of falling (No), the first determination section 425 determined that there is no event in the first body state of the subject (non-detection).

Further, in the processing S16, the first determination section 425 determines whether or not a last posture of the subject determined last time and stored in the posture record storage section 52 is the standing posture (S16). As a result, when it is determined that the last posture of the subject is the standing posture (Yes), the first determination section 425 performs processing S17. On the other hand, when it is determined that the last posture of the subject is not the standing posture (No), the first determination section 425 performs processing S18.

In the processing S17, the first determination section 425 determines whether or not a latest posture of the subject input this time from the posture detection section 422 is the standing posture (S17). As a result, when it is determined that the latest posture of the subject is the standing posture (Yes), the first determination section 425 determines that there is no event in the first body state of the subject (no-detection). On the other hand, when it is determined that the latest posture of the subject is not the standing posture (No), the first determination section 425 performs processing S19.

In the processing S19, the first determination section 425 determines whether or not a latest detection result (falling of the subject) input this time from the falling detection section 423 is the presence of falling (S19). As a result, when it is determined that the latest posture of the subject is the presence of falling (Yes), the first determination section 425 determines that the first body state of the subject is "fall-over". On the other hand, when it is determined that the latest posture of the subject is the absence of falling (No), the first determination section 425 determined that there is no event in the first body state of the subject (non-detection).

In the processing S18, the first determination section 425 determines whether or not a latest posture of the subject input this time from the posture detection section 422 is the standing posture (S18). As a result, when it is determined that the latest posture of the subject is the standing posture (Yes), the first determination section 425 determines that there is no event in the first body state of the subject (no-detection). On the other hand, when it is determined that the latest posture of the subject is not the standing posture (No), the first determination section 425 determines that the first body state of the subject is "fall-over".

Then, when the first body state of the subject is determined as "fall-off" as a first case, the first determination section 425 determines that the subject is in the abnormal state, and, when the first body state of the subject is determined as "fall-over" as a second case, the first determination section 425 determines that the subject is in the abnormal state. For example, among accidents in medical facility, a rate of fall-over and fall-off is relatively high. And, in the event of fall-over or fall-off, it is necessary to promptly take measures such as rescue activities. Therefore, in this embodiment, two situations where the first determination section 425 of the first body state determination unit 42 determines that the first body state of the subject is "fall-off" and "fall-over" are set as a condition for determining that the subject is in the abnormal state.

After determining the first body state of the subject based on the posture, the presence or absence of falling and the location of the subject detected, respectively, by the detection sections 422, 423, 424, the first determination section 425 outputs the determination result (in this embodiment, any one of "sitting-up", "out-of-bed", "fall-off", "fall-over"

and "no-event", and the presence or absence of the abnormal state of the subject) to each of the first and second ascertainment sections 441, 442.

After the determination about the first body state of the subject based on the image data from the image data generator MC is made by the first body state determination unit 42, or in concurrence with the determination process in the first body state determination unit 42, the second body state determination unit 43 determines the second body state of the subject based on the physiological data from the physiological data generator P1.

More specifically, first of all, the differential processing section 431 of the second body state determination unit 43 differentiates Doppler shift data as the physiological data of the subject, and outputs the differentiated Doppler shift data to the body motion detection section 432, as mentioned above. Then, the body motion detection section 432 counts the number of body motions on the assumption that one body motion occurs when the differentiated Doppler shift data is equal to or greater than the + body motion determination threshold and one body motion occurs when the differentiated Doppler shift data is equal to or less than the—body motion determination threshold, and calculates the number of counted body motions per unit time, as the body motion number. Then, the body motion detection section 432 outputs the calculated body motion number to the second determination section 435.

Along with this body motion number calculation processing, the FFT section 433 of the second body state determination unit 43 subjects the Doppler shift data as the physiological data of the subject to fast Fourier transformation to obtain a frequency distribution of the Doppler shift data, and outputs the obtained frequency distribution of the Doppler shift data to the respiration detection section 434, as mentioned above. Then, the respiration detection section 434 detects, as a respiratory fundamental component, a frequency component having a highest intensity (peak frequency component) in the frequency distribution of the Doppler shift data, and multiplies the respiratory fundamental component by 60 to obtain the respiratory rate per unit time. Then, the respiration detection section 434 outputs the obtained respiratory rate to the second determination section 435.

Subsequently, based on the body motion number and the respiration rate of the subject detected, respectively, by the detection sections 432, 434, the second determination section 435 determines the second body state of the subject. Specifically, the second determination section 435 determines that the subject is in the abnormal state, when the respiration detection section 434 determines, based on the respiration rate of the subject, that the subject is in an apneic state, and the body motion detection section 432 determines, based on the body motion number of the subject, that there was a body motion, as a third case, and determines that the subject is in the abnormal state, when the respiration detection section 434 determines, based on the respiration rate of the subject, that the subject is in a relatively-rapid respiration state, and the body motion detection section 432 determines, based on the body motion number of the subject, that there was a body motion, as a fourth case.

After determining the second body state of the subject based on the body motion number and the respiratory rate of the subject detected, respectively, by the detection sections 432, 434, the second determination section 435 outputs a result of the determination to each of the first and second ascertainment sections 441, 442 of the notification control unit 44.

When the determination result about the first body state of the subject is input from the first determination section 425 of the first body state determination unit 42, and the determination result about the second body state of the subject is input from the second determination section 435 of the second body state determination unit 43, the notification control unit 44 determines whether or not the subject's abnormal state-indicating notification should be issued.

More specifically, in FIG. 9, the notification control unit 44 ascertains whether or not each of the first and second body states of the subject determined by respective one of the first and second body state determination units 42, 43 is an abnormal state (S21). As a result, when it is ascertained that each of the first and second body states of the subject determined by respective one of the first and second body state determination units 42, 43 is an abnormal state (Yes), the notification control unit 44 performs processing S25. On the other hand, when it is determined that both of the first and second body states of the subject determined by respective ones of the first and second body state determination units 42, 43 are not entirely abnormal states (No), i.e., at least one of the first and second body state determination units 42, 43 determines that a corresponding at least one of the first and second body states of the subject is not an abnormal state (No), the notification control unit 44 performs processing S22.

In this embodiment, in the processing S21, the first ascertainment section 441 ascertains whether the first body state of the subject is the abnormal state A, and ascertains whether the second body state of the subject is the abnormal state B. As a result, when it is ascertained that the first body state of the subject determined by the first body state determination unit 42 is the abnormal state A, and the second body state of the subject determined by the second body state determination unit 43 is the abnormal state B (Yes in the processing S21), the first ascertainment section 441 outputs the information indicating that the subject is in the abnormal state, to the notification section 443, and thereby processing S25 is performed. In any case other than the above (No in the processing S21), the processing S22 is performed after the ascertainment. It should be noted that, when the first ascertainment section 441 ascertains whether or not the second body state of the subject is the abnormal state B, the second body state of the subject determined by the second body state determination unit 43 may be re-determined based on the location of the subject detected by the first body state determination unit 42. The second ascertainment section 442 ascertains whether or not the second body state of the subject is the abnormal state C, and ascertains whether or not the first body state of the subject is the abnormal state D. As a result, when it is ascertained that the second body state of the subject determined by the second body state determination unit 43 is the abnormal state C, and the first body state of the subject determined by the first body state determination unit 42 is the abnormal state D (Yes in the processing S21), the second ascertainment section 442 outputs the information indicating that the subject is in the abnormal state, to the notification section 443, and thereby the processing S25 is performed. In any case other than the above (No in the processing S21), the processing S22 is performed after the ascertainment. It should be noted that, when the second ascertainment section 442 ascertains whether or not the second body state of the subject is the abnormal state C, the second body state of the subject determined by the second body state determination unit 43 may be re-determined based on the location of the subject detected by the first body state determination unit 42. This applies to aftermentioned processing S23 and processing S24.

In the processing S22, the notification control unit 44 ascertains whether or not one of the first and second body states of the subject determined by a corresponding one of the first and second body state determination units 42, 43 is not an abnormal state. As a result, when it is ascertained that one of the first and second body states of the subject determined by a corresponding one of the first and second body state determination units 42, 43 is not an abnormal state (Yes), the notification control unit 44 performs processing S23. On the other hand, when the situation where one of the first and second body states of the subject determined by a corresponding one of the first and second body state determination units 42, 43 is not an abnormal state is not ascertained (No), i.e., when it is ascertained that both of the first and second body states of the subject determined by respective ones of the first and second body state determination units 42, 43 are not an abnormal state (No), the notification control unit 44 terminates the process. Alternatively, the process may be terminated after performing processing S31 indicated by the broken line in FIG. 9, as described later.

In this embodiment, in the processing S22, the first ascertainment section 441 ascertains whether or not the first body state of the subject determined by the first body state determination unit 42 is not the abnormal state A, and the second body state of the subject determined by the second body state determination unit 43 is the abnormal state B. As a result, when it is ascertain that the first body state of the subject determined by the first body state determination unit 42 is not the abnormal state A, and the second body state of the subject determined by the second body state determination unit 43 is the abnormal state B (Yes in the processing S22), the processing S23 is performed. On the other hand, in any case other than above (No in the processing S22), the process is terminated. The second body state determination unit 43 ascertains whether or not the second body state of the subject determined by the second body state determination unit 43 is not the abnormal state C, and the first body state of the subject determined by the first body state determination unit 42 is the abnormal state D. As a result, when it is ascertain that the second body state of the subject determined by the second body state determination unit 43 is not the abnormal state C, and the first body state of the subject determined by the first body state determination unit 42 is the abnormal state D (Yes in the processing S22), the processing S23 is performed. On the other hand, in any case other than above (No in the processing S22, the process is terminated.

In the processing S23, the notification control unit 44 operates to cause one of the first and second body state determination units 42 which has made a determination of non-abnormal state to re-perform the determination about the corresponding body state of the subject, and then ascertain whether or not an the corresponding body state of the subject is determined to be an abnormal state (S24). As a result, when it is ascertained that the corresponding body state of the subject is determined to be an abnormal state (Yes in the processing S24), the processing 25 is performed. On the other hand, when it is ascertained that the corresponding body state of the subject is not determined to be an abnormal state (No in the processing S24), the process is terminated. Alternatively, the process may be terminated after performing processing S31 indicated by the broken line in FIG. 9, as described later.

In this embodiment, in the processing S23, the first ascertainment section 441 operates to cause the first body state determination unit 42 to re-perform the determination about the first body state of the subject, for a given period of time or by a given number of times. Then, in the processing S24, the first ascertainment section 441 ascertains whether or not the first body state of the subject is determined to be the abnormal state A, within the given period of time or the given number of times. As a result, when it is ascertains that the first body state of the subject is determined to be the abnormal state A, within the given period of time or the given number of times (Yes in the processing S24), the processing S25 is performed. On the other hand, when it is ascertained that the first body state of the subject is not determined to be the abnormal state A (No in the processing S24), the process is performed. Further, in the processing S23, the second ascertainment section 442 operates to cause the second body state determination unit 43 to re-perform the determination about the second body state of the subject, for a given period of time or by a given number of times. Then, in the processing S24, the second ascertainment section 442 ascertains whether or not the second body state of the subject is determined to be the abnormal state C, within the given period of time or the given number of times. As a result, when it is ascertains that the second body state of the subject is determined to be the abnormal state C, within the given period of time or the given number of times (Yes in the processing S24), the processing S25 is performed. On the other hand, when it is ascertained that the second body state of the subject is not determined to be the abnormal state C (No in the processing S24), the process is performed.

In the processing S25, the notification control unit 44 creates an e-mail addressed to a relevant watcher and describing a message indicating that the subject is in the abnormal state, and then the process is terminated. In this embodiment, in the processing S25, when the first ascertainment section 441 outputs information indicating that the first body state of the subject is in the abnormal state, and the second ascertainment section 442 outputs information indicating that the second body state of the subject is in the abnormal state, the notification section 443 creates an e-mail addressed to a relevant watcher and describing a message indicating that the subject is in the abnormal state, and sends the e-mail to the watcher. Then, the process is terminated. Thus, in the subject monitoring system MS and the subject monitoring apparatus MD, a watcher carrying the communication terminal CT having a function of receiving e-mails can receive information indicating that a relevant subject is in an abnormal state, at any location within a range communicable with the subject monitoring apparatus MD.

In addition to or in place of the message, a link (URL) for referring to the image of the subject in a streaming manner may be described in an e-mail, as mentioned above. As above, the subject monitoring system MS and the subject monitoring apparatus MD are configured to send an image of a subject, so that a relevant watcher can refer to the subject's image so as to visually recognize the subject's abnormal state through the image. Generally, an amount of information contained in an image is greater than that contained in text. Thus, the subject monitoring system MS and the subject monitoring apparatus MD make it possible to allow the watcher to more accurately determine the subject's abnormal state and thus reduce an erroneous determination.

Further, at least one of the first and second body states of the subject may be described in the e-mail. In this case, the watcher can refer to such an e-mail to thereby recognize a cause (reason) for determination of the abnormal state, and recognize details of the abnormal state.

The process may be terminated after performing processing S31 indicated by the broken line in FIG. 9, as described below.

In the processing S31, the notification control unit 44 creates an e-mail addressed to the relevant watcher and describing any one of the first and second body states of the subject, and sends the e-mail to the watcher. Thus, the watcher can recognize the state of the subject even in a situation where the subject is not in the abnormal state. The processing in S31 is relatively frequently performed. Thus, the subject monitoring system MS may be configured to select whether or not an email set in the processing S31 from the communication terminal CT is received.

Each of the subject monitoring system MS, the subject monitoring apparatus MD, and a subject monitoring method implemented in the subject monitoring apparatus MD in this embodiment is configured to, when a subject is determined to be in an abnormal state, send a notification message indicating that the subject is in an abnormal state, to a relevant one of the communication terminals CT, so that it becomes possible to, when abnormality occurs in the subject, automatically issue a notification indicative of this fact. In a determination as to whether or not the subject is in the abnormal state, to be performed in advance of the automatic notification, each of the subject monitoring system MS, the subject monitoring apparatus MD, and the subject monitoring method is configured to not only determine the second body state of the subject, based on the physiological data of the subject, but also determine the first body state of the subject, based on the image data of the subject, so that it becomes possible to reduce an error in determination as to whether or not the subject is in the abnormal state. Each of the subject monitoring system MS, the subject monitoring apparatus MD, and the subject monitoring method is configured to, when one of the first and second body states of the subject, determined by a corresponding one of the first and second body state determination units 42, 43, is not an abnormal state, to cause the one of the first and second body state determination units to re-perform the determination, and then determine whether or not a notification indicating that the subject is in the abnormal state (subject's abnormal state-indicating notification) should be issued, based on a result of the determination about the one of first and second body states of the subject, re-performed by the one of the first and second body state determination units, so that it becomes possible to enhance performance for determining whether or not the subject is in the abnormal state (determination performance), and more adequately issue the subject's abnormal state-indicating notification.

In each of the subject monitoring system MS, the subject monitoring apparatus MD, and the subject monitoring method, it is ascertained that the body state of the subject determined by one of the first and second body state determination units 42, 43 is a first abnormal state (e.g., the abnormal state B or the abnormal state D), and then it is ascertained whether the body state of the subject determined by a remaining one of the first and second body state determination units 42, 43 is a second abnormal state (e.g., the abnormal state A or the abnormal state C) corresponding to the first abnormal state. Thus, in each of the subject monitoring system MS and the subject monitoring apparatus MD, the first and second body state determination units 42, 43b are configured to determine the same abnormal state or mutually-related abnormal states, so that it becomes possible to reduce an error in determination as to whether or not the subject is in the abnormal state.

Each of the subject monitoring system MS and the subject monitoring apparatus MD is configured to cause the remaining one of the first and second body state determination units 42, 43 to re-perform the determination about the corresponding body state of the subject, for a given period of time or by a given number of times, so that it becomes possible to enhance the determination performance, and reduce an error in determination as to whether or not the subject is in the abnormal state.

Each of the subject monitoring system MS and the subject monitoring apparatus MD is configured to, during the determination as to whether or not the subject's abnormal state-indicating notification should be issued, to re-determine the second body state of the subject determined by the second body state determination unit 43, based on the location of the subject detected by the first body state determination unit 42.

Specifically, as described in connection with the processing S22 to the processing S24, during the determination as to whether or not the subject's abnormal state-indicating notification should be issued, one of the image data-based determination result of the first body state determination unit 42, and the physiological data-based determination result of the second body state determination unit 43 is used for ascertaining a remaining one of the determination results, so that it becomes possible to reduced the erroneous determination. In other words, the image data-based determination result of the first body state determination unit 42 may be ascertained by continuously using the physiological data-based determination result of the second body state determination unit 43, wherein, when consistency with the image data-based determination result of the first body state determination unit 42 is ascertained, the notification is performed, and, when the consistency is not ascertained, the notification is canceled. Conversely, the physiological data-based determination result of the second body state determination unit 43 may be ascertained by continuously using the image data-based determination result of the first body state determination unit 42, wherein, when consistency with the physiological data-based determination result of the second body state determination unit 43 is ascertained, the notification is performed, and, when the consistency is not ascertained, the notification is canceled.

For example, in a situation where a body motion is observed by the second body state determination unit 43 based on he physiological data, and fall-over is also detected in a location other than the bed by the first body state determination unit 42 based on the image data, or in a situation where a body motion is observed by the second body state determination unit 43 based on he physiological data, and fall-off is detected in a location other than the bed by the first body state determination unit 42 based on the image data, the notification is performed at a time when it is ascertained that the fall-over or fall-off is correct. On the other hand, in a situation where a body motion is observed by the second body state determination unit 43 based on he physiological data, and the subject is detected in a location of the bed by the first body state determination unit 42 based on the image data, it is deemed that a cloth, futon or the like falls from the bed, and this is erroneously determined as fall-over or fall-off, and thus the notification is cancelled. In this manner, the second abnormal state corresponding to the given first abnormal state determined as the body state of the subject by one of the first and second body state determination units is re-determined by a remaining one of the first and second body state determination units, so that it becomes possible to reduce an erroneous detection.

For example, when a cloth, futon or the like is moved, this movement is likely to be extracted as a person region, because a size thereof is similar to that of a person. Thus, if fall-over or fall-off is determined only by the image date, there is a risk that falling of a cloth, futon or the like is erroneously determined as fall-over or fall-off. In a situation where only a region of a cloth or futon extracted as a person region on the bed falls from the bed, independently of the subject on the bed, based on the image data, the first body state determination unit 42 determines the cloth or futon region at a position to which the cloth or futon falls downwardly from the bed, and, particularly when the cloth or futon falls from the bed with a small vertical-to-horizontal ratio, determines that the subject falls from the bed in a lying posture, resulting in erroneous determination. For example, in a situation where a portion of a futon slips down to a floor while a remaining portion of the futon stays on the bed, whereafter this falling state gradually progresses and finally the futon entirely falls from the bed, the first body state determination unit 42 determines that falling occurs after leaving from the bed, i.e., determines the situation as "fall-over", resulting in erroneous determination. In a situation where the subject takes off his/her clothes, it can be erroneously determined as fall-over or fall-off. However, each of the subject monitoring system MS, the subject monitoring apparatus MD and the subject monitoring method in this embodiment can operate as mentioned above, so that it becomes possible to reduce such erroneous determinations.

Further, for example, the first body state determination unit 42 is operable, when it determines, based on the image data, that the subject is located on the bed, to enable the second body state determination unit 43 to determine an abnormal state based on the physiological data. Supposing that the subject is absence, an apneic state is detected and the second body state determination unit 43 determines the state as an abnormal state based on the physiological data. However, the second body state determination unit 43 can be enabled to determine an abnormal state based on the physiological data when the first body state determination unit 42 determines, based on the image data, that the subject is located on the bed, and can be disabled to determine an abnormal state based on the physiological data when the first body state determination unit 42 determines, based on the image data, that the subject is located out of the bed.

Further, when the second body state determination unit 43 determines, based on the physiological data, that the subject is in the abnormal state, in teens of respiratory rate, the first body state determination unit 42 checks, based on the image data, whether or not the subject is located on the bed. When the subject is located only on the bed at that time, it is determined that abnormal respiration definitely occurs in the subject on the bed, and thus the notification is performed. On the other hand, when it is determined that the subject is also located out of the bed, in addition to the location on the bed, at that time, there is a possibility that the physiological data generator P1 acquires, as the physiological data, respiration of the subject together with respiration of a caregiver or the like, and thus the second body state determination unit 43 determines that the subject is in the abnormal state, based on the physiological data, i.e., respiration of a plurality of persons. For this reason, the second body state determination unit 43 can be enabled to determines, based on the physiological data, that the subject is in the abnormal state, in terms of respiratory rate, at a time when the first body state determination unit 42 determines, based on the image data, that the subject is located only on the bed. Further, in a situation where the first body state determination unit 42 determines, based on the image data, that the subject is located only out of the bed, and the second body state determination unit 43 determines, based on the physiological data, that abnormal respiration occurs, there is a possibility that the first body state determination unit 42 determines, based on the image data, that the subject leaves from the bed, but the second body state determination unit 43 is not disabled to determine, based on the physiological data, that the subject is in the abnormal state, in terms of respiratory rate. In this case, the second body state determination unit 43 can also be enabled to determines, based on the physiological data, that the subject is in the abnormal state, in terms of respiratory rate, at a time when the first body state determination unit 42 determines, based on the image data, that the subject is located only on the bed. This configuration makes it possible to reduce erroneous determinations, and more reliably determine only the abnormal state of the subject located on the bed, in terms of respiratory rate.

In the above embodiment, the image data generator MC includes one camera, and the subject monitoring apparatus MD is configured to determine the posture, location and falling of a subject from an image of one point-of-view of the one camera. Alternatively, the image data generator MC may include a pair of right and left cameras (stereo camera), and the subject monitoring apparatus MD may be configured to determine the posture, location and falling of a subject from a three-dimensional image of the stereo camera.

In the above embodiment, the first body state determination unit 42 is configured to determine one of "sitting-up", "out-of-bed", "fall-off", "fall-over" and "no-event" of the subject. In addition to them or in place of a part or an entirety of them, other suitable notion may be determined. Further, for simplifying information processing in the first body state determination unit 42, the first body state determination unit 42 may be configured to determine only "fall-over" and "fall-off" which are particularly important.

In the above embodiment, when issuing a notification indicating that the subject is in the abnormal state, a difference in degree of urgency may be set in nursing care for the subject, the subject monitoring apparatus MD is configured to change a content of the subject's abnormal state-indicating notification, depending on the degree of urgency, may be configured to change a coverage of relevant watchers who receive the subject's abnormal state-indicating notification, depending on the degree of urgency. For example, a situation where, in an initial determination, the first and second body state determination units 42, 43 determine that the respective first and second body states are abnormal states is deemed that the degree of urgency is relatively high, and the subject monitoring apparatus MD is operable to describe, in an e-mail, a message indicating that the subject is in the abnormal state, and a link (URL) for referring to the image of the subject in a streaming manner, and deliver the e-mail to a plurality of watchers. The plurality of watchers may be a plurality of nurses or may be a plurality of caregivers, or may be a nurse and a medical doctor. On the other hand, for example, a situation where, in an initial determination, one of the first and second body state determination units 42, 43 determines that a corresponding one of the first and second body states is an abnormal state is deemed that the degree of urgency is relatively low, and the subject monitoring apparatus MD is operable to describe, in an e-mail, a message indicating that the subject is in the abnormal state, without describing a link (URL) for referring to the image of the subject in a streaming manner, considering privacy of the subject, and deliver the e-mail to a relevant watcher. As above, a warning notification may be issued in a hierarchical way. In this case, when the degree of urgency is relatively low, the subject monitoring apparatus MD and the subject monitoring system MS can issue a warning notification with a focus on privacy of the subject, and, when the degree of urgency is relatively low, the subject monitoring apparatus MD and the subject monitoring system MS can issue a warning notification with a focus on clearly informing a relevant watcher of a situation of the subject, rather than privacy of the subject. Based on such two types of warning notifications, the subject monitoring apparatus MD and the subject monitoring system MS can issue a more considerate and satisfactory warning notification to the subject and a relevant watcher.

This specification discloses techniques having various aspects. Among them, major techniques will be outlined below.

According to a first aspect, there is provided a subject monitoring apparatus which includes: an image data input unit for inputting image data of a subject to be monitored; a physiological data input unit for inputting physiological data of the subject; a first body state determination unit operable, based on the image data of the subject input from the image data input unit, to determine a first body state of the subject; a second body state determination unit operable, based on the physiological data of the subject input from the physiological data input unit, to determine a second body state of the subject; and a notification control unit operable, to issue a notification indicating that the subject is in an abnormal state, when the each of the first and second body states of the subject determined by respective ones of the first and second body state determination units is the abnormal state, and to cause the one of the first and second body state determination units to re-perform the determination, and then determine whether or not the subject's abnormal state-indicating notification should be issued, based on a result of the determination about the one of first and second body states of the subject by the one of the first and second body state determination units, when one of the first and second body states of the subject, determined by a corresponding one of the first and second body state determination units, is not an abnormal state.

The subject monitoring apparatus having the above feature is configured to, when the subject is determined to be in the abnormal state, issue a notification indicating that the subject is in the abnormal state, so that it becomes possible to, when abnormality occurs in the subject, automatically issue a notification indicative of this fact. In a determination as to whether or not the subject is in the abnormal state, to be performed in advance of the automatic notification, the subject monitoring apparatus is configured to not only determine the second body state of the subject, based on the physiological data of the subject, but also determine the first body state of the subject, based on the image data of the subject, so that it becomes possible to reduce an error in determination as to whether or not the subject is in the abnormal state. The subject monitoring apparatus is configured to, when one of the first and second body states of the subject, determined by a corresponding one of the first and second body state determination units, is not an abnormal state, to cause the one of the first and second body state determination units to re-perform the determination, and then determine whether or not the subject's abnormal state-indicating notification should be issued, based on a result of the determination about the one of first and second body states of the subject, re-performed by the one of the first and second body state determination units, so that it becomes possible to enhance performance for determining whether or not the subject is in the abnormal state, and more adequately issue the subject's abnormal state-indicating notification.

Preferably, in the above subject monitoring apparatus, the notification control unit is operable, in response to ascertaining a situation where the body state of the subject determined by one of the first and second body state determination units is a given first abnormal state, and the body state of the subject determined by a remaining one of the first and second body state determination units is a second abnormal state corresponding to the first abnormal state, as the situation where each of the body states of the subject determined by respective ones of the first and second body state determination units is an abnormal state, to issue the subject's abnormal state-indicating notification In the subject monitoring apparatus having this feature, it is ascertained that the body state of the subject determined by one of the first and second body state determination units is a first abnormal state, and then it is ascertained whether the body state of the subject determined by a remaining one of the first and second body state determination units is a second abnormal state corresponding to the first abnormal state. Thus, in this subject monitoring apparatus, the first and second body state determination units are configured to determine the same abnormal state or mutually-related abnormal states, so that it becomes possible to reduce an error in determination as to whether or not the subject is in the abnormal state.

More preferably, in the above subject monitoring apparatus, the notification control unit is operable, in response to ascertaining a situation where the body state of the subject determined by one of the first and second body state determination units is the first abnormal state, and the body state of the subject determined by a remaining one of the first and second body state determination units is not the second abnormal state corresponding to the first abnormal state, as the situation where one of the first and second body states, determined by a corresponding one of the first and second body state determination units, is not an abnormal state, to cause the remaining one of the first and second body state determination units to re-perform the determination about the corresponding body state of the subject, for a given period of time or by a given number of times, and then determine whether or not the subject's abnormal state-indicating notification should be issued, wherein the notification control unit is operable, when the corresponding body state of the subject is determined to be the second abnormal state, within the given period of time or the given number of times, to issue the subject's abnormal state-indicating notification.

The subject monitoring apparatus having this feature is configured to cause the remaining one of the first and second body state determination units to re-perform the determination about the corresponding body state of the subject, for a given period of time or by a given number of times, so that it becomes possible to enhance the determination performance, and reduce an error in determination as to whether or not the subject is in the abnormal state.

Preferably, in any one of the above subject monitoring apparatus of the present invention, the first body state determination unit is operable, based on the image data of the subject, to further detect a location of the subject, and wherein the notification control unit is operable, during the determination as to whether or not the subject's abnormal state-indicating notification should be issued, to re-determine the second body state of the subject determined by the second body state determination unit, based on the location of the subject detected by the first body state determination unit.

The subject monitoring apparatus having this feature is configured to, during the determination as to whether or not the subject's abnormal state-indicating notification should be issued, to re-determine the second body state of the subject determined by the second body state determination unit, based on the location of the subject detected by the first body state determination unit, so that it becomes possible to enhance the determination performance, and reduced the erroneous determination.

Preferably, in any one of the above subject monitoring apparatus, the physiological data is data representing a Doppler-shifted reflected wave of a microwave obtained by emitting the microwave to the subject.

The subject monitoring apparatus having this feature is capable of determining the body state of the subject based on each of the image data of the subject and data representing a reflected micro wave reflected by the subject, so that the body state of the subject can be determined in a non-contact manner.

Preferably, in any one of the above subject monitoring apparatus, the notification control unit is operable to issue the subject's abnormal state-indicating notification to a watcher via e-mail.

The subject monitoring apparatus having this feature is capable of sending the subject's abnormal state-indicating notification to a relevant watcher via e-mail. Thus, in this subject monitoring apparatus, a watcher carrying the communication terminal having a function of receiving e-mails, such as a mobile phone, a smartphone, or a tablet computer, can receive information indicating that a relevant subject is in an abnormal state, at any location within a range communicable with the subject monitoring apparatus.

Preferably, in any one of the above subject monitoring apparatus of the present invention, the notification control unit is operable to send an image of the subject as the subject's abnormal state-indicating notification, or further send an image of the subject together with the subject's abnormal state-indicating notification.

The subject monitoring apparatus having this feature is configured to send the image of the subject, so that a relevant watcher can refer to the image of the subject so as to visually recognize the abnormal state of the subject through the image. Generally, an amount of information contained in an image is greater than that contained in text. Thus, the subject monitoring apparatus make it possible to allow the watcher to more accurately determine the abnormal state of the subject and thus reduce the erroneous determination.

According to another aspect, there is provided a subject monitoring method which includes: an image data accepting step of accepting image data of a subject to be monitored; a physiological data accepting step of accepting physiological data of the subject; a first body state determination step of, based on the image data of the subject accepted in the image data accepting step, determining a first body state of the subject; a second body state determination step of, based on the physiological data of the subject accepted in the physiological data accepting step, determining a second body state of the subject; and a notification control step of, issuing a notification indicating that the subject is in an abnormal state, when each of the first and second body states of the subject determined in respective one of the first and second body state determination steps is an abnormal state, and re-performing the determination in the one of the first and second body state determination steps, and then determining whether or not the subject's abnormal state-indicating notification should be issued, based on a result of the determination about the corresponding body state of the subject in the one of the first and second body state determination steps, when one of the first and second body states of the subject, determined in a corresponding one of the first and second body state determination steps, is not an abnormal state.

The subject monitoring method having the above feature is configured to, when the subject is determined to be in the abnormal state, issue a notification indicating that the subject is in the abnormal state, so that it becomes possible to, when abnormality occurs in the subject, automatically issue a notification indicative of this fact. In a determination as to whether or not the subject is in the abnormal state, to be performed in advance of the automatic notification, the subject monitoring method is configured to not only determine the second body state of the subject, based on the physiological data of the subject, but also determine the first body state of the subject, based on the image data of the subject, so that it becomes possible to reduce an error in determination as to whether or not the subject is in the abnormal state. The subject monitoring method is configured to, when one of the first and second body states of the subject, determined by a corresponding one of the first and second body state determination units, is not an abnormal state, to cause the one of the first and second body state determination units to re-perform the determination, and then determine whether or not the subject's abnormal state-indicating notification should be issued, based on a result of the determination about the one of first and second body states of the subject, re-performed by the one of the first and second body state determination units, so that it becomes possible to enhance performance for determining whether or not the subject is in the abnormal state, and more adequately issue the subject's abnormal state-indicating notification.

According to yet another aspect, there is provided a subject monitoring system which includes: an image data generator configured to generate image data of a subject to be monitored; a physiological data generator configured to generate physiological data of the subject; and any one of the above subject monitoring apparatus, wherein the subject monitoring apparatus is configured such that the image data of the subject generated by the image data generator is input into the image data input unit, and the physiological data of the subject generated by the physiological data generator is input into the physiological data input unit.

The subject monitoring system having the above feature is configured to, when the subject is determined to be in the abnormal state, issue a notification indicating that the subject is in the abnormal state, so that it becomes possible to, when abnormality occurs in the subject, automatically issue a notification indicative of this fact. In a determination as to whether or not the subject is in the abnormal state, to be performed in advance of the automatic notification, the subject monitoring system is configured to not only determine the second body state of the subject, based on the physiological data of the subject, but also determine the first body state of the subject, based on the image data of the subject, so that it becomes possible to reduce an error in determination as to whether or not the subject is in the abnormal state. The subject monitoring system is configured to, when one of the first and second body states of the subject, determined by a corresponding one of the first and second body state determination units, is not an abnormal state, to cause the one of the first and second body state determination units to re-perform the determination, and then determine whether or not the subject's abnormal state-indicating notification should be issued, based on a result of the determination about the one of first and second body states of the subject, re-performed by the one of the first and second body state determination units, so that it becomes possible to enhance performance for determining whether or not the subject is in the abnormal state, and more adequately issue the subject's abnormal state-indicating notification.

This application is based on Japanese Patent Application Serial No. 2013-190185 filed in Japan Patent Office on Sep. 13, 2013, the contents of which are hereby incorporated by reference.

Although the present invention has been described appropriately and fully by way of the embodiment as above with reference to the drawings in order to express the present invention, it should be appreciated that anyone skilled in the art can readily change and/or modify the embodiment described above. It is therefore understood that a changed embodiment or a modified embodiment implemented by anyone skilled in the art is encompassed within the scope of the appended claims unless the changed embodiment or the modified embodiment is of a level that deviates from the scope of the appended claims.

INDUSTRIAL APPLICABILITY

The present invention can provide a subject monitoring apparatus, a subject monitoring method and a subject monitoring method.

The invention claimed is:

1. A subject monitoring apparatus comprising:
an image data input unit for inputting image data of a subject to be monitored;
a physiological data input unit for inputting physiological data of the subject;
a first body state determination unit operable, based on the image data of the subject input from the image data input unit, to determine a first body state of the subject as being one of a normal state and an abnormal state;
a second body state determination unit operable, based on the physiological data of the subject input from the physiological data input unit, to determine a second body state of the subject as being one of the normal state and the abnormal state; and,
a notification control unit operable to:
in a case in which each of the first and second body states of the subject determined by the first and second body state determination units, respectively, is the abnormal state, issue a notification indicating that the subject is in the abnormal state, and
in a case in which one of the first and second body states of the subject, determined by the first and second body state determination units, respectively, is not the abnormal state, cause whichever of the first and second body state determination units that made the not abnormal state determination to re-perform the determination, and then determine whether or not the subject's abnormal state-indicating notification should be issued, based on a result of the re-performed determination.

2. The subject monitoring apparatus as recited in claim 1, wherein the notification control unit is operable, in response to ascertaining a situation where the body state of the subject determined by one of the first and second body state determination units is a given first abnormal state, and the body state of the subject determined by a remaining one of the first and second body state determination units is a second abnormal state corresponding to the first abnormal state, as the situation where each of the body states of the subject determined by respective ones of the first and second body state determination units is an abnormal state, to issue the subject's abnormal state-indicating notification.

3. The subject monitoring apparatus as recited in claim 2, wherein the notification control unit is operable, in response to ascertaining a situation where the body state of the subject determined by one of the first and second body state determination units is the first abnormal state, and the body state of the subject determined by a remaining one of the first and second body state determination units is not the second abnormal state corresponding to the first abnormal state, as the situation where one of the first and second body states, determined by a corresponding one of the first and second body state determination units, is not an abnormal state, to cause the remaining one of the first and second body state determination units to re-perform the determination about the corresponding body state of the subject, for a given period of time or by a given number of times, and then determine whether or not the subject's abnormal state-indicating notification should be issued, wherein the notification control unit is operable, when the corresponding body state of the subject is determined to be the second abnormal state, within the given period of time or the given number of times, to issue the subject's abnormal state-indicating notification.

4. The subject monitoring apparatus as recited in claim 1, wherein the first body state determination unit is operable, based on the image data of the subject, to further detect a location of the subject, and wherein the notification control unit is operable, during the determination as to whether or not the subject's abnormal state-indicating notification should be issued, to re-determine the second body state of the subject determined by the second body state determination unit, based on the location of the subject detected by the first body state determination unit.

5. The subject monitoring apparatus as recited in claim 1, wherein the physiological data is data representing a Doppler-shifted reflected wave of a microwave obtained by emitting the microwave to the subject.

6. The subject monitoring apparatus as recited in claim 1, wherein the notification control unit is operable to issue the subject's abnormal state-indicating notification to a watcher via e-mail.

7. The subject monitoring apparatus as recited in claim 1, wherein the notification control unit is operable to send an image of the subject as the subject's abnormal state-indicating notification, or further send an image of the subject together with the subject's abnormal state-indicating notification.

8. A subject monitoring method comprising:
an image data accepting step of accepting image data of a subject to be monitored;
a physiological data accepting step of accepting physiological data of the subject;
a first body state determination step of, based on the image data of the subject accepted in the image data accepting step, determining a first body state of the subject as being one of a normal state and an abnormal state;
a second body state determination step of, based on the physiological data of the subject accepted in the physiological data accepting step, determining a second body state of the subject as being one of the normal state and the abnormal state; and a notification control step of, in a case in which each of the first and second body states of the subject determined by the first and second body state determination steps, respectively, is the abnormal state, issuing a notification indicating that the subject is in the abnormal state, and in a case in which one of the first and second body states of the subject, determined by the first and second body state determination steps, respectively, is not the abnormal state, causing whichever of the first and second body state determination steps that made the not abnormal state determination to re-perform the determination, and then determining whether or not the subject's abnormal state-indicating notification should be issued, based on a result of the re-performed determination.

9. A subject monitoring system comprising:

an image data generator configured to generate image data of a subject to be monitored;

a physiological data generator configured to generate physiological data of the subject; and the subject monitoring apparatus as recited in claim 1, wherein the subject monitoring apparatus is configured such that the image data of the subject generated by the image data generator is input into the image data input unit, and the physiological data of the subject generated by the physiological data generator is input into the physiological data input unit.

10. A subject monitoring apparatus comprising:

an image data input unit for inputting image data of a subject to be monitored;

a first body state determination unit, based on the image data of the subject input from the image data input unit, to determine a first body state of the subject;

a physiological data input unit for inputting physiological data of the subject;

a second body state determination unit, based on the physiological data of the subject input from the physiological data input unit, to determine a second body state of the subject; and a notification control unit, configured to:

issue a notification indicating that the subject is in an abnormal state, when each of the first and second body states of the subject determined by respective ones of the first and second body state determination units is the abnormal state, and in response to ascertaining a situation where the body state of the subject determined by one of the first and second body state determination units is a given first abnormal state, and the body state of the subject determined by a remaining one of the first and second body state determination units is not a second abnormal state corresponding to the first abnormal state, cause the remaining one of the first and second body state determination units to re-perform the determination for a given period of time or a given number of times, and issue the subject's abnormal state-indicating notification when the corresponding body state of the subject is determined to be the second abnormal state within the given period of time or the given number of times.

11. A subject monitoring apparatus comprising:

a plurality of monitoring units adapted to provide respective data resulting from monitoring of the subject;

a plurality of body state determination units operable, in response to said data of the subject from said plurality of monitoring units, respectively, to determine a body state of the subject as being either a normal state or an abnormal state; and a notification control unit operable to:

(i) issue a notification indicating that the subject is in an abnormal state, when each of the body states determined by said plurality of body state determination units is the abnormal state, and (ii) if the body state determined by at least one of the plurality of body state determination units is not the abnormal state, cause the at least one of the plurality of body state determination units to re-perform the determination, and then issue a notification that the subject is in the abnormal state, based on a result of the re-performed determination, if each of the body states determined by said plurality of body state determination units is the abnormal state.

* * * * *